(12) United States Patent
Sakurai

(10) Patent No.: US 7,731,677 B2
(45) Date of Patent: Jun. 8, 2010

(54) ULTRASONIC SURGICAL SYSTEM

(75) Inventor: Tomohisa Sakurai, Hachioji (JP)

(73) Assignee: Olympus Corporation (JP)

( * ) Notice: Subject to any disclaimer, the term of this patent is extended or adjusted under 35 U.S.C. 154(b) by 252 days.

(21) Appl. No.: 10/849,699

(22) Filed: May 19, 2004

(65) Prior Publication Data

US 2004/0215131 A1 Oct. 28, 2004

Related U.S. Application Data

(62) Division of application No. 09/482,791, filed on Jan. 13, 2000, now abandoned.

(30) Foreign Application Priority Data

| Jan. 19, 1999 | (JP) | ............................ 11-010822 |
| Mar. 19, 1999 | (JP) | ............................ 11-076333 |
| Sep. 22, 1999 | (JP) | ............................ 11-269242 |

(51) Int. Cl.
*A61B 17/20* (2006.01)
(52) U.S. Cl. ...................................... 604/22
(58) Field of Classification Search ............. 604/22; 606/41, 42, 34
See application file for complete search history.

(56) References Cited

U.S. PATENT DOCUMENTS

| 3,809,977 | A | * | 5/1974 | Balamuth et al. ............ 318/116 |
| 5,342,356 | A | * | 8/1994 | Ellman et al. ................. 606/34 |
| 5,391,144 | A | * | 2/1995 | Sakurai et al. ................ 604/22 |
| 5,455,766 | A | * | 10/1995 | Scheller et al. ................ 606/4 |
| 5,562,503 | A | * | 10/1996 | Ellman et al. ............... 439/638 |
| 5,685,821 | A | * | 11/1997 | Pike ............................ 600/118 |
| 6,017,354 | A | * | 1/2000 | Culp et al. ................... 606/170 |
| 6,036,458 | A | * | 3/2000 | Cole et al. ................... 604/111 |

FOREIGN PATENT DOCUMENTS

| JP | 04-231037 A | 5/1993 |
| JP | 05-111502   | 5/1993 |
| JP | 06-343647   | 12/1994 |
| JP | 9-38098     | 2/1997 |

\* cited by examiner

*Primary Examiner*—Kevin C Sirmons
*Assistant Examiner*—Elizabeth R Moulton
(74) *Attorney, Agent, or Firm*—Ostrolenk Faber LLP

(57) ABSTRACT

An ultrasonic surgical system enables connection of a hand switch as well as a foot switch, which is used to operate a driving signal generator, without the necessity of retrofitting a main unit including the driving signal generator used to drive an ultrasonic transducer incorporated in a connected handpiece. An extension unit is included for connecting the foot switch and hand switch to the main unit. The foot switch and hand switch are connected to the main unit via the extension unit.

11 Claims, 16 Drawing Sheets

FIG.10
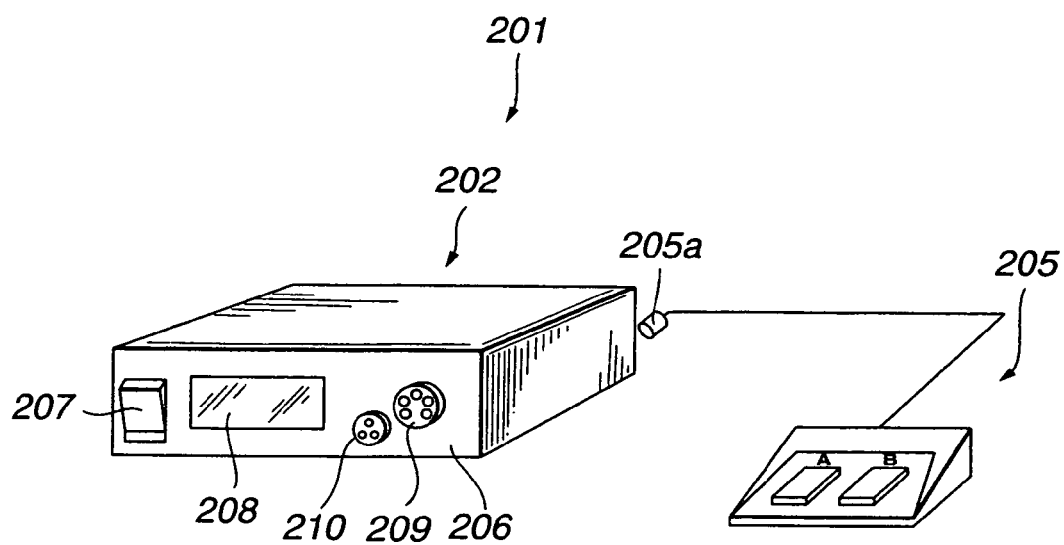
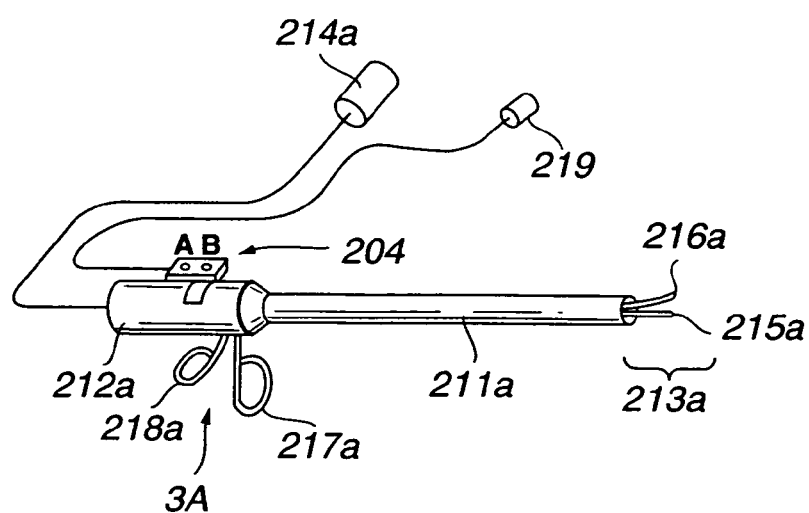

ULTRASONIC SURGICAL SYSTEM

CROSS-REFERENCE TO RELATED APPLICATIONS

The present application is a divisional under 37 C.F.R. §1.53(b) of prior application Ser. No. 09/482,791 filed Jan. 13, 2000 now abandoned by Tomohisa SAKURAI entitled ULTRASONIC SURGICAL SYSTEM.

BACKGROUND OF THE INVENTION

1. Field of the Invention

The present invention relates to an ultrasonic surgical system for treating a living tissue using ultrasonic waves generated by an ultrasonic transducer incorporated in a handpiece.

2. Description of the Related Art

Surgical apparatus utilizing ultrasonic waves have replaced electric cauterizing devices in various applications. For example, an ultrasonic knife unit and an ultrasonic trocar-and-cannula unit are described in Japanese Unexamined Patent Publication No. 9-38098, and are widely known.

This sort of ultrasonic surgical apparatus has a handpiece, in which an ultrasonic transducer is incorporated, connected to a main unit which includes a driving signal generator for generating an ultrasonic driving signal and a control unit. The ultrasonic transducer is driven to oscillate using the driving signal output from the main unit, whereby ultrasonic waves are generated. The generated ultrasonic waves are propagated into a treatment unit incorporated in the distal part of the handpiece. The treatment unit is pressed against a region to be treated, whereby a living tissue is treated.

For treating a living tissue using the ultrasonic surgical apparatus, the treatment unit in the handpiece is placed into contact with a region to be treated. A foot switch is employed to activate or deactivate the treatment unit.

However, for complex surgery, various types of foot switch operated equipment are used, and many foot switches may be present in the operating room. An operator must therefore be careful as not to press an incorrect foot switch, which is a source of distraction.

Moreover, depending on the procedure being performed, a plurality of different handpieces must be required. Different handpieces can therefore be selected and connected to the main unit of an ultrasonic surgical apparatus. The handpieces are changed depending on a purpose of use and thus used for different purposes.

Each main unit has a handpiece connector. For different handpieces, the connectors must be changed and a selected connector must be connected to the main unit every time it is needed. This, too, can be a nuisance, and also time consuming, which might be critical in the case of emergency medical services. As an alternative, a plurality of main units may be provided with the necessary handpieces connected to the main units in advance. This is wasteful of both money and space. Moreover, the user must select from the plurality of available handpieces to locate the one required. This, too, is a distraction.

Alternatively, it is conceivable to connect a plurality of handpieces to one main unit. In this case, a switching device is required for switching the connected handpieces. However, the main unit is often located in a non-sterile area, so the user cannot handle the switching device. The operator must therefore ask a nurse or the like to do so, and it becomes a nuisance to have to switch the handpieces.

Furthermore, some handpieces may have a perfusion channel and a suction channel formed therein. The perfusion channel is used to supply physiological saline with which a treated region is washed or cooled, while the suction channel is used to remove fragments of tissue pulverized using ultrasonic waves, together with physiological saline from the treatment unit. For such a handpiece, a perfusing and sucking capability must be incorporated in the main unit. In addition, a perfusion tube and a suction tube are needed for linking the main unit and the handpiece.

SUMMARY OF THE INVENTION

An object of the present invention is to provide an ultrasonic surgical system offering improved maneuverability of handpieces and operator convenience. Another object is to provide an ultrasonic surgical system which can be activated or inactivated using a hand switch or a foot switch.

Another object of the present invention is to provide an ultrasonic surgical system enabling connection of a plurality of handpieces to one main unit without the necessity of retrofitting the main unit. Even when a plurality of handpieces are needed for an operation, it is unnecessary to provide a plurality of main units in an operating room.

Still another object of the present invention is to provide an ultrasonic surgical system offering improved maneuverability. The ultrasonic surgical system makes it possible to activate or inactivate respective handpieces connected to a main unit, and to use the plurality of connected handpieces for different purposes.

According to the present invention, there is provided an ultrasonic surgical system having a main unit that includes a driving signal generator, an output unit, a manipulation signal sensing unit, a control unit, and a manipulation signal input unit. The driving signal generator generates, a driving signal used to drive an ultrasonic transducer in a handpiece. The output unit transmits the driving signal generated by the driving signal generator to the ultrasonic transducer in the handpiece. The manipulation signal sensing unit senses an input manipulation signal. The control unit controls the driving signal generator according to the manipulation signal sensed by the manipulation signal sensing unit. The manipulation signal input unit provides the manipulation signal.

The ultrasonic surgical system includes an extension unit having an input unit for providing the manipulation signal by means of a connected hand switch or foot switch. The extension unit also includes an output unit for outputting the manipulation signal input to the input unit and based on a manipulation performed on the hand switch or the foot switch to the manipulation signal input unit in the main unit.

Moreover, according to the present invention, there is provided an ultrasonic surgical system having a main unit that includes a driving signal generator, an output unit, manipulation signal sensing unit, a control unit, and manipulation signal input unit. The driving signal generator generates a driving signal to drive the ultrasonic transducer in a handpiece. The output unit provides the driving signal generated by the driving signal generator to the ultrasonic transducer in the handpiece. The manipulation signal sensing unit senses an input manipulation signal. The control unit controls the driving signal generator according to the manipulation signal sensed by the manipulation signal sense unit. The manipulation signal input unit provides the manipulation signal.

The ultrasonic surgical system has an extension unit including an input unit for inputting a driving signal, plurality of output units, a switching unit, an input unit for inputting a manipulation signal, and an output unit. The input unit for inputting a driving signal is connected to the driving signal output unit in the main unit. The plurality of output units outputs the driving signal input to the driving signal input unit to ultrasonic transducers in a plurality of handpieces. The switching unit switches the plurality of output units to select an output unit for outputting a driving signal. The input unit for inputting a manipulation signal has at least one of a hand switch and foot switch, which generate the manipulation signal, connected thereto. The output unit outputs the signal input to the manipulation signal input unit to the manipulation signal input unit in the main unit.

Furthermore, according to the present invention, there is provided an ultrasonic surgical system having a main unit that includes a driving signal generator, an output unit, a manipulation signal sense unit, a control unit, and a manipulation signal input unit. The driving signal generator generates a driving signal used to drive and oscillate an ultrasonic transducer in a handpiece. The output unit outputs a driving signal generated by the driving signal generator and destined for the ultrasonic transducer in the handpiece. The manipulation signal sense unit senses an input manipulation signal. The control unit controls the driving signal generator according to the manipulation signal sensed by the manipulation signal sense unit. The manipulation signal input unit inputs the manipulation signal. Ultrasonic waves stemming from the ultrasonic transducer incorporated in the handpiece are propagated in order to operate a living tissue.

The ultrasonic surgical system has an extension unit including an input unit for inputting a driving signal, a plurality of output units, a switching unit, an input unit for inputting a manipulation signal, and an output unit. The input unit for inputting a driving signal is connected to the driving signal output unit in the main unit. The plurality of output units outputs the driving signal input to the driving signal input unit to ultrasonic transducers in a plurality of handpieces. The switching unit switches the plurality of output units to select an output unit for outputting a driving signal. The input unit for inputting a manipulation signal is connected tout least one of a hand switch and a foot switch that produces the manipulation signal. The output unit outputs the signal input to the manipulation signal input unit to the manipulation signal input unit in the main unit.

Furthermore, according to the present invention, a perfusing means, a sucking means, and a communicating and controlling means are included. The perfusing means supplies a fluid to a handpiece through a perfusion tube.

The sucking means sucks a pulverized tissue and a fluid from the handpiece through a suction tube. The communicating and controlling means allowing the main unit and extension unit to communicate with each other and give control so that when a n ultrasonic suction handpiece is selected, at least one of said perfusing means and sucking means will be actuated synchronously with output of ultrasonic waves.

Other features and advantages of the present invention will be fully apparent from the description below.

BRIEF DESCRIPTION OF THE DRAWINGS

FIG. 10 is an explanatory diagram schematically showing the configuration of an ultrasonic surgical system in accordance with the fourth embodiment of the present invention;

DESCRIPTION OF THE PREFERRED EMBODIMENTS

Figure 1:
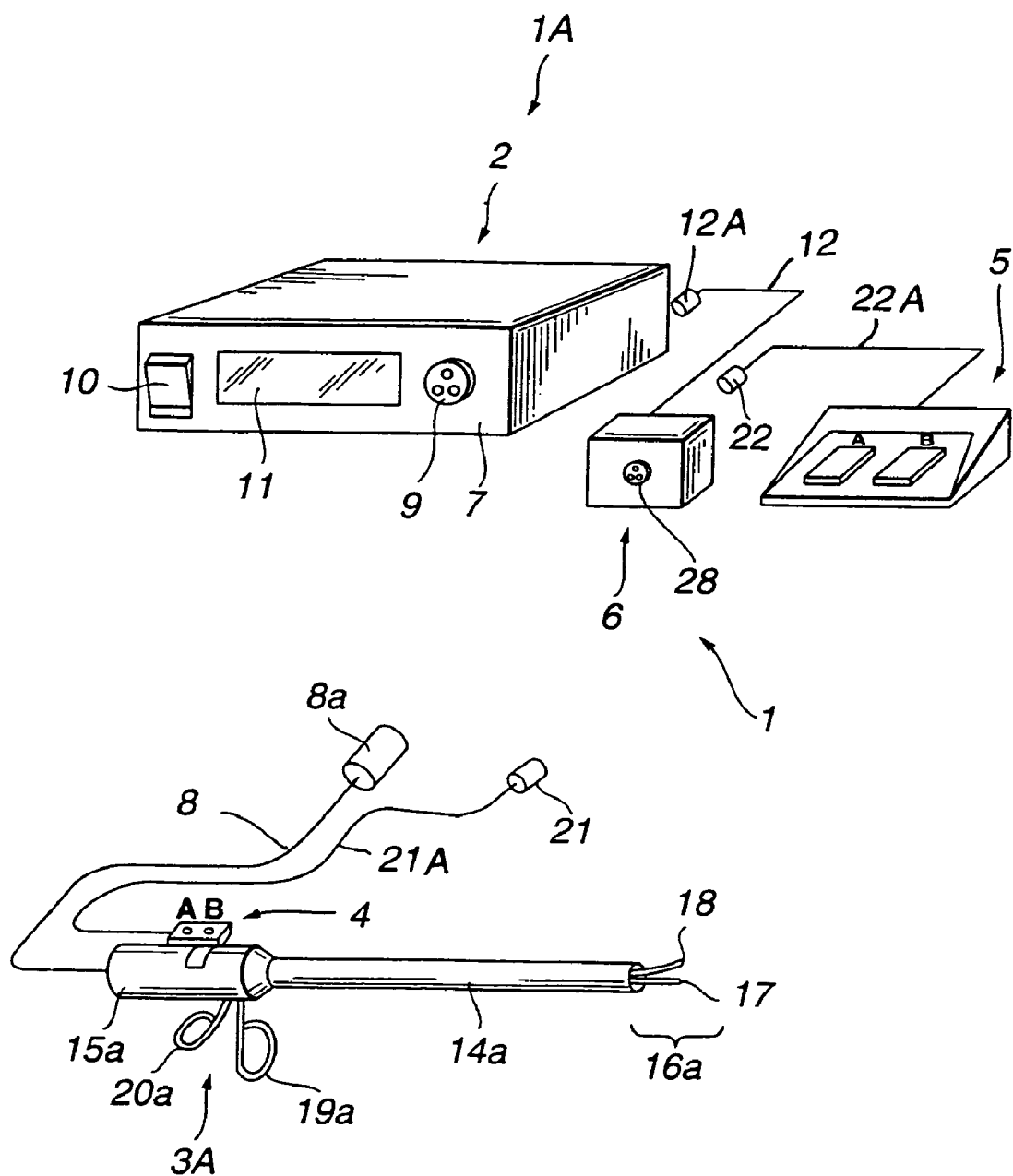
FIG. 1 is an explanatory diagram schematically showing the configuration of an ultrasonic surgical system in accordance with the first embodiment of the present invention having a scissors-like handpiece.
Figure 2A:
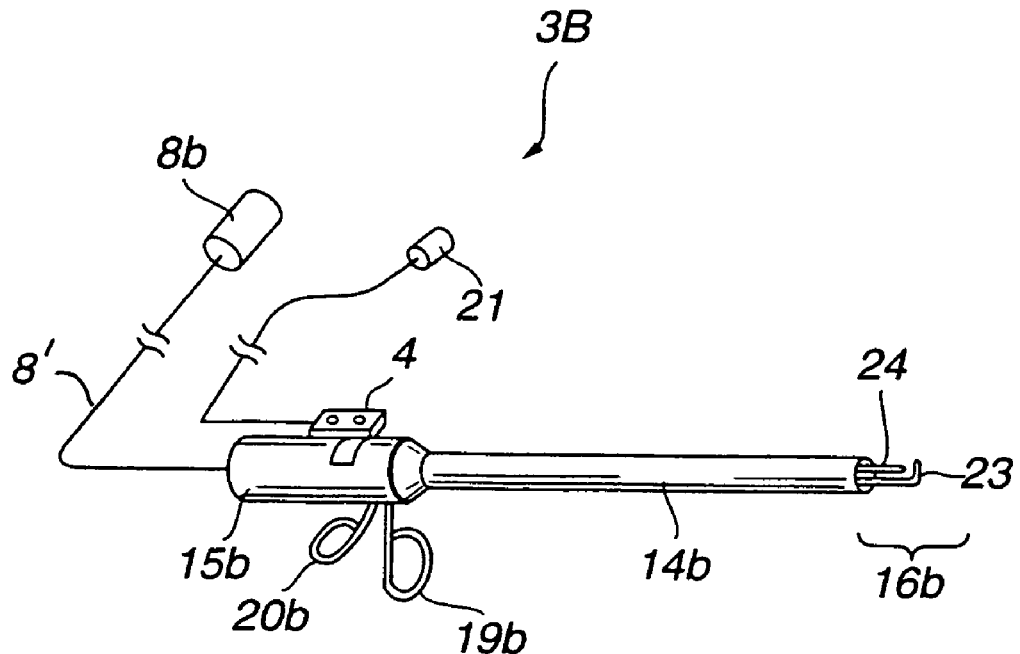
FIG. 2A and FIG. 2B are explanatory diagrams respectively showing a hook-like handpiece and a trocar and cannula-like handpiece.
Figure 2B:
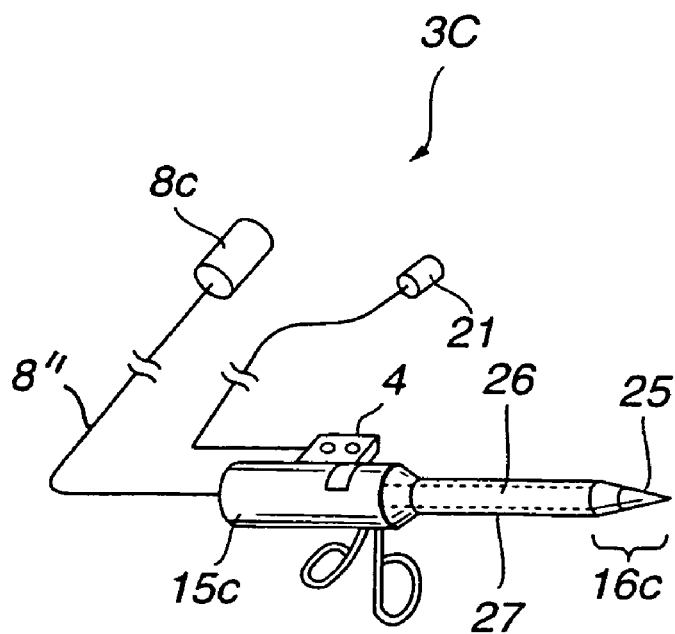
Figure 3:
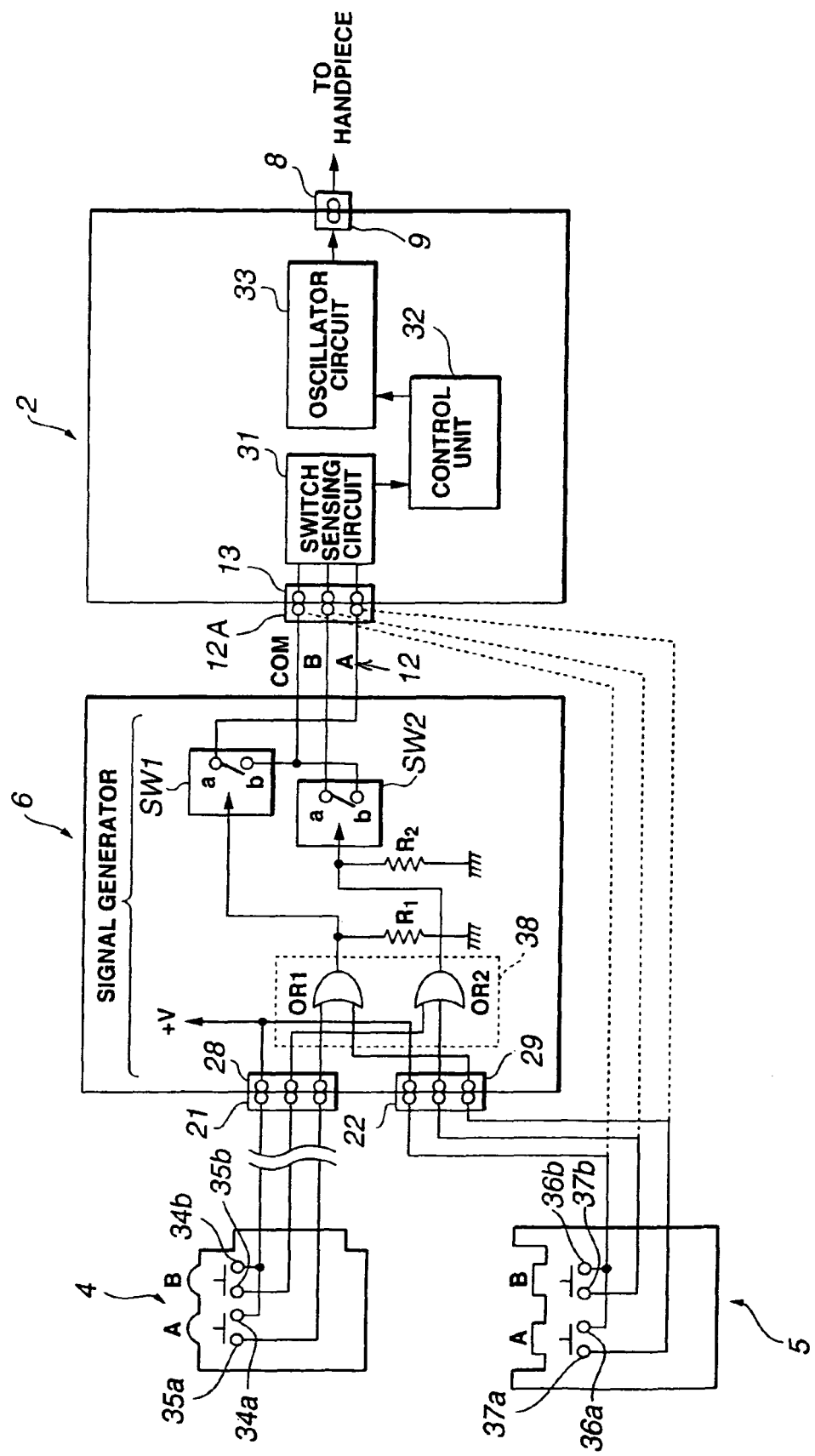
FIG. 3 is a circuit block diagram showing circuits included in a hand switch, a foot switch, an extension unit, and a main unit.
Figure 4:
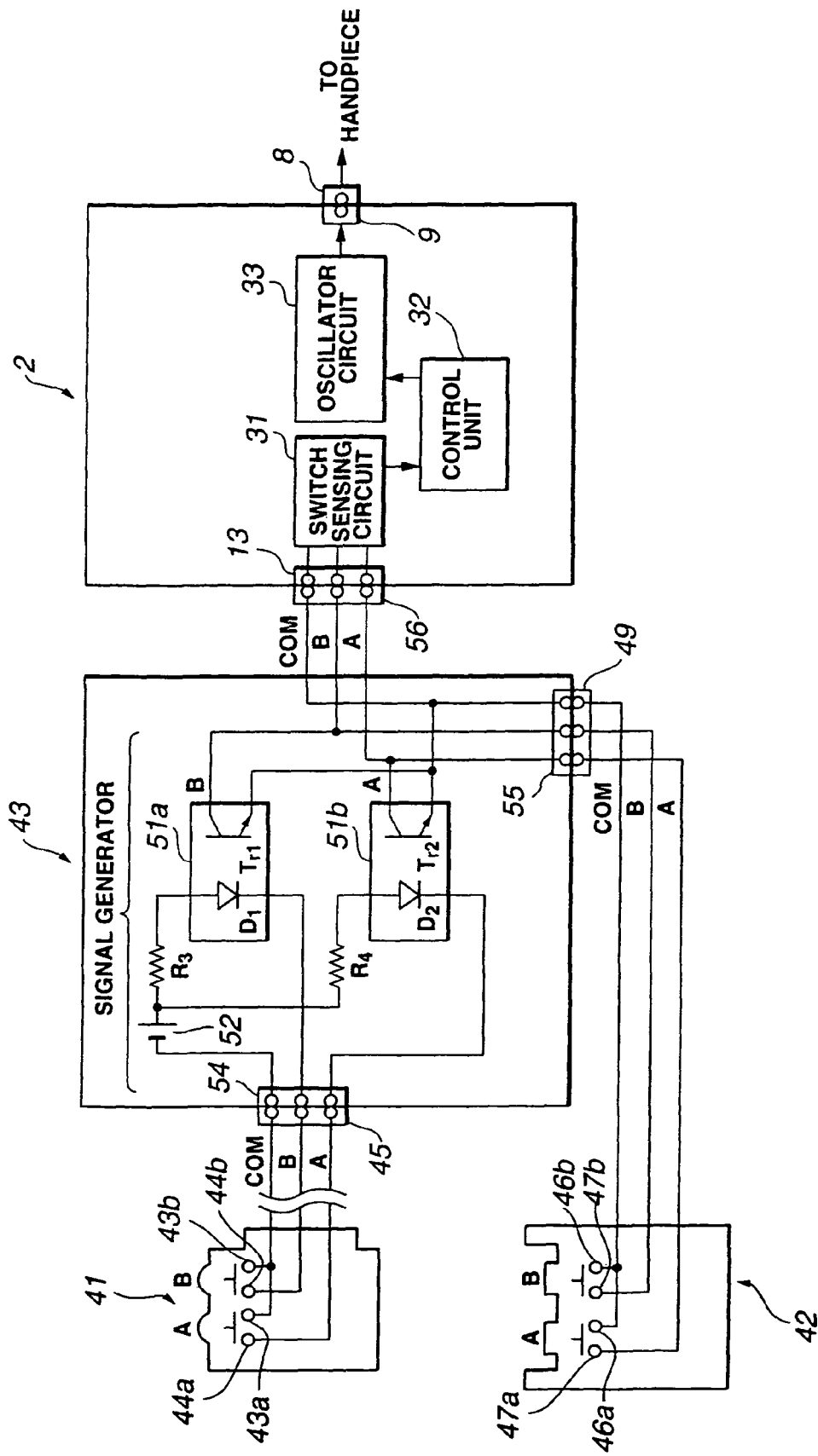
FIG. 4 is a circuit block diagram of another embodiment of circuits such as shown in FIG. 3.

FIG. 1 to FIG. 4 relate to the first embodiment of the present invention. FIG. 1 is an explanatory diagram schematically showing the configuration of an ultrasonic surgical system having a scissors-like handpiece" which is a first handpiece, connected to a main unit so that the handpiece can be unconnected freely. FIG. 2A and FIG. 2B are explanatory diagrams showing second and third handpieces connected to the main unit as alternatives to the scissors-like handpiece shown in FIG. 1. FIG. 2A shows the appearance of a hook-like handpiece, while FIG. 2B shows a trocar and cannula-like handpiece that is the third handpiece. FIG. 3 is a circuit block diagram showing circuits incorporated in the hand switch, a foot switch, an extension unit, and the main unit which are shown in FIG. 1. FIG. 4 is a circuit block diagram for explaining examples of circuits different from those shown in FIG. 3.

An ultrasonic surgical system 1 of the present embodiment has, as an ultrasonic surgical apparatus 1A, a main unit 2, a scissors-like handpiece 3A, a hand switch 4, a foot switch 5, and an extension unit 6. The main unit 2 has a driving signal generator, which is used to drive an ultrasonic transducer (not shown), incorporated therein. The scissors-like handpiece 3A is connected to the main unit 2 and includes a second ultrasonic transducer (also not shown), incorporated therein. The hand switch 4 is detachably mounted on handpiece 3A. The foot switch 5 is also provided, and may be used instead of the hand switch 4.

An extension unit 6 has a manipulation signal generator operated by hand switch 4 or foot switch 5 to produce a manipulation signal. A cable 12 and a connector 12A transmit the manipulation signal to the main unit 2.

A handpiece connector portion 9, a power switch 10, and a display panel 11 are arranged on a front panel 7 of the main unit 2. A handpiece connector portion 8a connected to the handpiece 3A by a suitable cable 8 is adapted to mate with handpiece connector portion 9. The power switch 10 is used to turn on or off the power supply of the main unit. The display panel 11 displays the moving situation of the scissors-like handpiece 3A. When handpiece connector portions 8a and 9 are coupled together, the main unit 2 enables ultrasonic treatment. A joint connector portion 13 As best illustrated in FIG. 3, a connector portion 13, which may be located on the back of main portion 2 is adapted to mate with connector portion 12A, and serves to connect extension unit 6 to main unit 2 over cable 12.

Handpiece 3A is comprised of an elongated sheath 14a, an operation unit 15a coupled to the proximal end of the sheath 14a, and a treatment unit 16a located in the distal end of the sheath 14a.

An ultrasonic transducer for generating ultrasonic waves (not shown), and a probe 17 for propagating the ultrasonic waves generated by the ultrasonic transducer are incorporated handpiece 3A. The treatment unit 16a has a clamping portion 18 supported to freely pivot at the distal end of the sheath 14a. The operating unit 15a has a stationary handle 19a and a movable handle 20a. The movable handle 20a is opened or closed relative to the stationary handle 19a, whereby the clamping-portion 18 of the treatment unit 16a can be brought into contact with or separated from the distal part of the probe 17. In this case, when the movable handle 20a is closed, the clamping portion 18 is turned in a direction in which the clamping portion 18 is closed relative to the distal part of the probe 17. The clamping portion 18 and the distal part of the probe 17 cooperate with each other, for example, to claim a blood vessel. In this state, the ultrasonic transducer in handpiece 3A is driven in order to ultrasonically coagulate or incise the living tissue clamped by the probe 17 and clamping portion 18.

The hand switch 4 is detachably mounted on operating unit 15a. The hand switch 4 may consist, for example, of two switches A and B. A connector 21, linked to the switches A and B by a cable 21A is adapted to mate with a connector 28 on extension unit 6.

Likewise, the foot switch 5 may be comprised of two pedal switches A and B used to control activation or inactivation of the ultrasonic transducer. A switch connector 22 linked to the switches by a cable 22A mates with a connector 29 on extension unit 6 (see FIG. 3).

A hook-like handpiece 3B shown in FIG. 2A includes a treatment unit 16b, extending from a sheath 14b, and an attached operating unit 15b. Similarly to the scissors-like handpiece 3A, a hand switch 4 is detachably mounted on operating unit 15B.

The treatment unit 16b of the hook-like handpiece 3B has a substantially L-shaped receptor 23 fixed to the distal end of the sheath 14b, and an abutment member 24 capable of sliding axially in the sheath 14b. The distal part of a probe (not shown) is coupled to either the receptor 23 or abutment member 24.

A movable handle 20b is opened or closed relative to a stationary handle 19b of the operating unit 15b, whereby the abutment member 24 can be brought into contact with or separated from the receptor 23. In this case, when the movable handle 20 is closed, the abutment member 24 of the treatment unit 16b is slid to abut on the receptor 23. The abutment member 24 and receptor 23 cooperate with each other in clamping a living tissue, for example, a blood vessel.

The ultrasonic transducer in handpiece 3B is driven in this state, whereby the living tissue clamped by the abutment member 24 and receptor 23 is treated ultrasonically.

A trocar and cannula-like handpiece A shown in FIG. 2B, is designed to mechanically oscillate a needle connected to the ultrasonic transducer (not shown) and thus cause the needle to pierce the wall of a body cavity.

Handpiece 3C consists of an elongated needle 25, an armor 27, an operating unit 15c, and a treatment unit 16c. The needle 25 pierces the wall of a body cavity while propagating oscillatory energy produced by the ultrasonic transducer. The armor 27 has a guide hole 26 through which the needle 25 is passed. The operating unit 15c is coupled to the proximal end of the needle 25. The treatment unit 16c is the proximal part of the needle 25.

The hand switch 4 is detachably mounted on operating unit 15c of the handpiece 3C similarly to that of the scissors-like handpiece 3A.

The trocar and cannula-like handpiece 3C is used after the epidermis of a body cavity is partially incised using a knife of the like. Specifically, the treatment unit 16c of the trocar and cannula-like handpiece 3C is thrust into the wall of a body cavity. The needle 25 is oscillated using the ultrasonic transducer, whereby the needle applies piercing force to the wall of a body cavity together with the armor 27 mated with the needle due to the guide hole 26. The needle 25 is thus thrust forward to pierce a tissue. After the armor 27 is also thrust into the tissue, the needle 25 is withdrawn with the armor 27 remaining in the wall of the body cavity. An endoscope (not shown) or any other treatment appliance may then be inserted into the guide hole 26 of the armor 27 in order to observe or operate on a lesion. Similarly, to handpiece 3A, handpiece 3B is connected to main unit 2 by a cable 8' through a releasable connector portion 8b. Handpiece 3C is connected to main unit 2 by a cable 8" through a releasable connector portion 8c.

Referring again to FIG. 1, a signal produced by a manipulation signal generator described below incorporated in the extension unit 6 is transmitted to the main unit 2 through cable 12 and connector 12A. The hand switch 4 is connected to the main unit 2 via the extension unit 6. When either switch A or B of the hand switch 4 is pressed, the movement of, for example, the selected and connected scissors-like handpiece 3A can be controlled.

In the illustrated embodiment, when the extension unit 6 is connected to the main unit 2, hand switch 4 as well as the foot switch 5 can be connected to the main unit without the necessity of retrofitting the main unit 2. Consequently, an operator would enjoy improved maneuverability.

Referring to FIG. 3, a description will be made of the circuitry of the ultrasonic surgical system consisting of the hand switch 4 and foot switch 5, the extension unit 6 to which the connectors linked to the hand switch 4 and foot switch 5 are joined, and the main unit 2 to which the extension unit 6 is connected.

The main unit 2 includes a switch sensing circuit 31, a control unit 32, and an oscillator circuit 33. The switch sensing circuit 31 detects a signal sent from the foot switch 5 or hand switch 4 via the extension unit 6. The control unit 32 outputs a control signal according to a signal output from the switch sensing circuit 31. The oscillator circuit 33 drives the handpiece according to the control signal output from the control unit 32. As previously noted, a connector portion 13 mounted on main unit 2 mates with connector portion 12A to couple main unit 2 to the extension unit 6 over cable 12, while connector portion 9 to which the handpiece connectors 8a 8b, and 8c on the ends of respective cables 8, 8' and 8", may be connected, links one of the handpieces such as 3A, 3B or 3C to the main unit 2. Foot switch connector 22 linked to the foot switch 5 may be joined directly to the main unit 2. In this case, the switch sensing circuit 31 in the main unit 2 can receive a signal derived from either of the two pedal switches A and B of the foot switch 5 which is stepped on.

The hand switch 4 consists of, for example, the aforesaid two switches A and B, and has the hand switch connector 21 linked thereto. The hand switch connector 21 accommodates a line linking a contact 34a of the switch A and a contact 34b of the switch B, a line linked to a contact 35a of the switch A, and a line linked to a contact 35b of the switch B.

When the switch A of the hand switch 4 is pressed, the contacts 34a and 3A of the switch A close and complete an electrical circuit to the extension unit 6 via the hand switch connector 21. When the switch B is pressed, the contacts 34b and 35b of the switch B close and complete a circuit to the extension unit 6 via the hand switch connector 21.

The foot switch 5 consists of, for example, the aforesaid two pedal switches A and B. The circuitry of the foot switch is analogous to that of the hand switch 4. Specifically, a contact 36a of the pedal switch A and a contact 36b of the pedal switch B are linked, and a contact 37a of the pedal switch A and a contact 37b of the pedal switch B are linked.

The manipulation signal generator of the extension unit 6 may include, for example, a circuit composed of one OR gate OR1 of an OR circuit 38 and an analog switch SW1 and a circuit composed of a second OR gate OR2 of the OR circuit 38 and an analog switch SW2. The analog switch SW1 opens or closes based on an output of the OR gate OR1. The analog switch SW2 opens or closes based on an output of the OR gate OR2. As mentioned previously, the extension unit 6 has the hand switch connector portion 28, the foot switch connector portion 29, and the joint connector 12. The hand switch connector 21 of the hand switch 4 is joined to the hand switch connector portion 28. The foot switch connector 22 of the foot switch 5 is joined to the foot switch connector portion 29. The joint connector 12 serves as a connecting means for connecting the extension unit to the main unit 2.

Among three lines accommodated by the hand switch connector portion 28 of the extension unit 6, the first line is linked to a voltage source +V used to bring a signal to a high level and to the foot switch connector portion 29 to which the foot switch connector 22 is joined. The second line is linked to the OR gate OR1. The third line is linked to the OR gate OR2.

Similarly, in foot switch connector portion 29, a first line is linked to the voltage source +V used to bring a signal to a high level and to the hand switch connector portion 28 to which the hand switch connector 21 is joined. The second line is linked to the OR gate OR1, and the third line is linked to the OR gate OR2.

The output terminal of the OR gate OR1 is connected t the analog switch SW1. The output terminal of the OR gate OR2 is connected to the analog switch SW2. The node between the OR gate OR1 and analog switch SW1 and the node between the OR gate OR2 and analog switch SW2 are grounded via a resistor R1 and a resistor R2 respectively. When the switch A or B of the hand switch 4 is not pressed or the switch A or B of the foot switch 5 is not stepped on, the output terminal of the OR gate OR1 or OR gate OR2 is low.

A contact a of the analog switch SW1 is connected to a contact A of connector 12. A contact b thereof is connected to a contact COM of connector 12. A contact a of the analog switch SW2 is connected to a contact B of connector 12, and a contact b thereof is connected to the contact COM of connector 12.

When the hand switch 4 is pressed or the foot switch 5 is stepped on, either the hand switch 4 or foot switch 5 conducts. Either of the two OR gates OR1 and OR2 becomes active via the hand switch connector 21 of the hand switch 4 or the foot switch connector 22 of the foot switch 5. Either the analog switch SW1 or analog switch SW2 is turned on and conducts electricity to the switch sensing circuit 31 in the main unit via the contacts A and COM of the joint connector 12 or the contacts B and COM thereof. More particularly, when the switch A of the hand switch 4 is pressed, the contact 34a and contact 35a of the switch A conduct to go high due to the voltage source +V in the extension unit. This causes the OR gate OR1 to conduct. The analog switch SW1 makes an on-to-off transition. When the analog switch SW1 is turned on, the analog switch SW1 conducts electricity to the contacts A and COM of the joint connector 12. The switch A of the hand switch 4, the OR gate ORI of the extension unit 6, the analog switch SW1, and the contacts A and 60M of the joint connector 12 constitute a closed circuit. Consequently, the switch sense circuit 31 senses that the switch A of the hand switch 4 has been pressed. The extension unit 6 may be designed to deal with the hand switch 4 or foot switch 5 as a top priority or to deal with a switch manipulated first as a top priority.

When the switch A or B of the hand switch 4 is pressed, a signal is transmitted to the extension unit 6. An output of the extension unit 6 is transmitted to the switch sensing circuit 31 in the main unit 2. It is then sensed which of the switches has been pressed. Based on a sensed signal, the control unit 32 activates or deactivates the oscillator circuit 33. An output of the oscillator circuit 33 is transmitted to handpiece 3A via the handpiece connector 3a.

Consequently, even when the ultrasonic apparatus 1A is designed to permit use of the foot alone, the hand switch 4 is usable. This leads to user-friendliness.

The hand switch 4 described in conjunction with FIG. 3 and the main unit 2 are electrically connected to each other. Thus, during treatment, when unit 16a of handpiece 3A is abutted on a region to be treated, there is a possibility that electricity may be conducted to the living tissue via the hand switch 4.

A circuit for electrically separating a hand switch 41 from a foot switch 42 may be, as shown in FIG. 4, included in an extension unit 43. To begin with, the hand switch 41 and foot switch 42 will be described below.

The hand switch 41 may include, like switch 4 shown in figure two switches A and B. A hand stitch connector 45 is linked to the hand switch 41. The hand switch connector 45 accommodates a line linking a contact 43a of the switch A and a contact 43b of _the switch B, a line linked to a contact 44a of the switch A, and a 'line linked to a contact 44b of the switch B.

The foot switch 42 may have the same components as the hand switch 41, and may include, for example, two pedal switches A and B. A foot switch connector 49 is linked to the foot switch 42 in the same manner as the hand switch connector linked to the hand switch 41. The foot switch connector 49 accommodates a line linking a contact 46a of the pedal switch A and a contact 46b of the pedal switch B, a line linked to a contact 47a of the pedal switch A, and a line linked to a contact 47b of the pedal switch B.

The extension unit 43 consists of two photocouplers 51a and 51b, a power source 52, and resistors R3 and R4. The photocouplers 51a and 51b electrically separate and isolate the hand switch 41 from the main unit 2 but still transmit signals. The power source 52 supplies power to the photocouplers 51a and 51b. The resistors R3 and R4 restrict a source current. The extension unit 43 has a hand switch connector portion 54 and a foot switch connector portion 55 formed thereon and has a connector 56 linked thereto. The hand switch connector 45 linked to the hand switch 41 is joined to the hand switch connector portion 54. The foot switch connector 49 linked to the foot switch 42 is joined to the foot switch connector portion 55. The connector 56 serves as a connecting means for-connecting the extension unit to the main unit 2.

One of lines accommodated by the hand switch connector portion 54 is linked to the power source 52. One end of the line is linked to a light emitting diode D1 in the photocoupler 51a via the resistor R3, and returned to the hand switch connector portion 54 from the light emitting diode D1. The other end thereof is linked to a light emitting diode D2 of the photocoupler 51b via the resistor R4, and returned to the hand switch connector portion 54 from the light emitting diode D2.

The output terminal of a phototransistor Tr1 for receiving light emitted from the light emitting diode D1 of the photocoupler 51a is connected to the connector 56 to be joined to the main unit 2 and to the foot switch connector portion 55 to which the foot switch connector 49 linked to the foot switch 42 is joined. The output of a phototransistor Tr2 for receiving light emitted from the light emitting diode D2 of the photocoupler 51b is also connected to the joint connector 56 and foot switch connector portion 55.

Thus, when the switch A or B of the hand switch 41 is pressed, the photocoupler 51a or 51b is actuated. This causes the switch sensing circuit 31 in the main unit 2 to operate, and ultrasonic waves are generated. When the pedal switch A or B of the foot switch 42 is stepped on, these components operate similarly. Since the hand switch and switch sense circuit are isolated from each other by the photocouplers 51a and 51b, a conductive path to the body part under treatment via the hand switch 41 can not exist.

Owing to the aforesaid components, the hand switch 41 and main unit 2 can be electrically separated from each other. The hand switch 41 can be used with a living tissue electrically secured more reliably than when a hand switch is used in combination with the circuits shown in FIG. 3.

In the ultrasonic surgical system of the present embodiment, the scissors-like handpiece 3A, hook-like handpiece 3B, and trocar and cannula-like handpiece 3C may be easily connected to and disconnected from one main unit 2 to perform ultrasonic treatment. However, the present invention is not limited to this mode. Any other handpiece, for example, handpiece for ultrasonically clipping an incised region by utilizing ultrasonic waves may be attached to the main unit 2.

Figure 5:
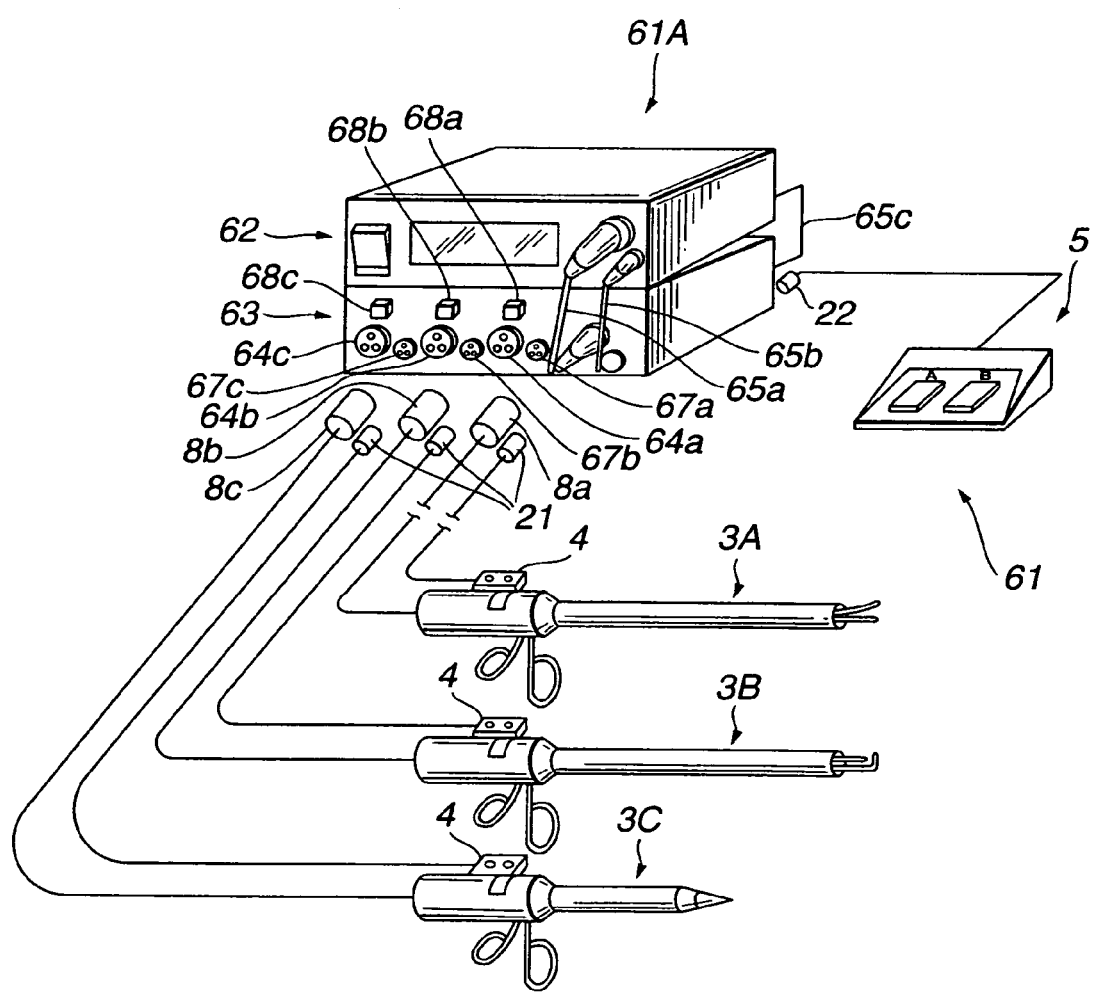
FIG. 5 is an explanatory diagram schematically showing the configuration of an ultrasonic surgical system in accordance with a second embodiment of the present invention.
Figure 6:
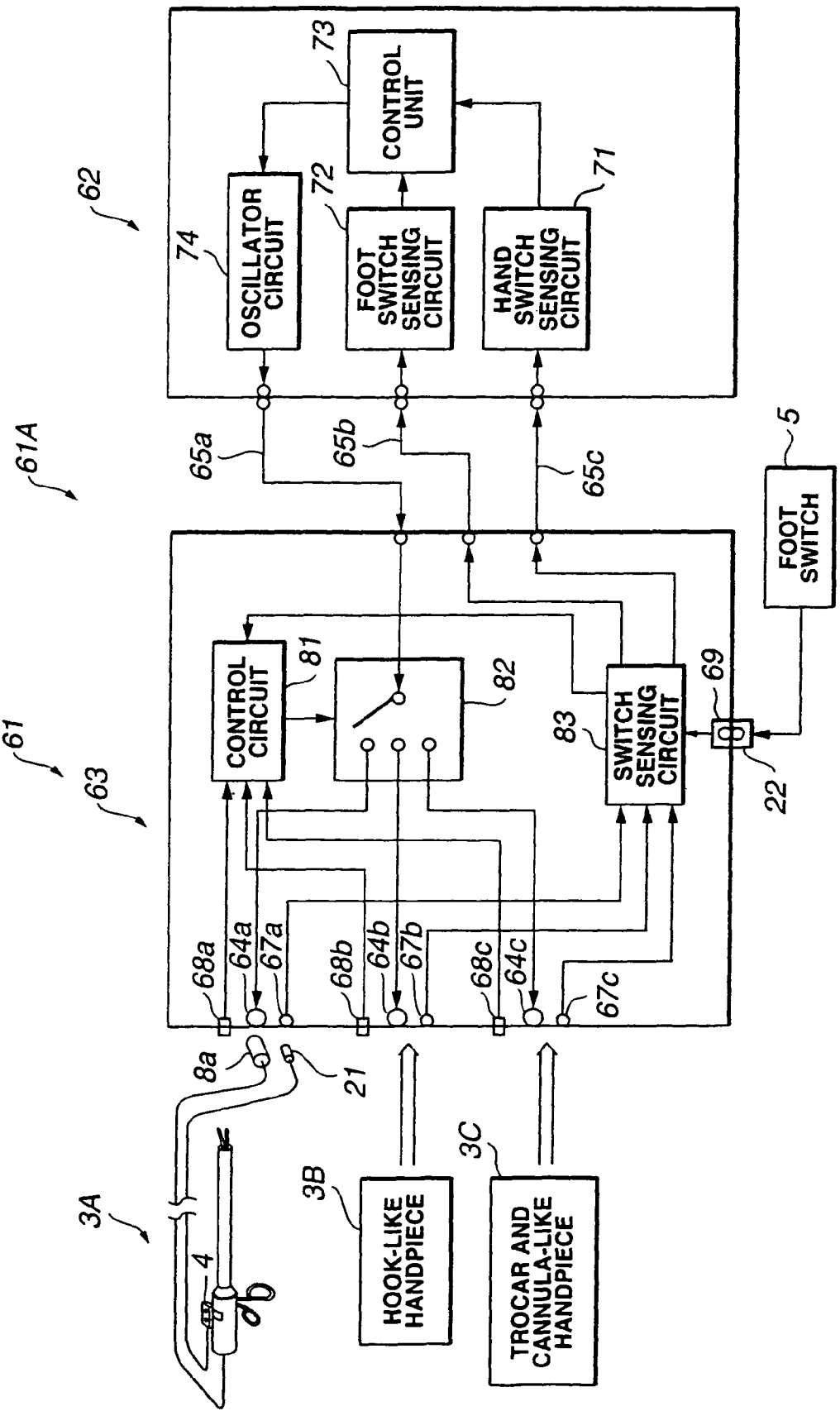
FIG. 6 is a block diagram showing circuitry suitable for use with the ultrasonic surgical system shown in FIG. 5.

FIG. 5 and FIG. 6 relate to a second embodiment of the present invention. FIG. 5 is an explanatory diagram schematically showing the configuration of an ultrasonic surgical system. The ultrasonic surgical system uses an ultrasonic surgical apparatus having a scissors-like handpiece, a hook-like handpiece, and a trocar and cannula-like handpiece, which are the first, second, and third handpieces, selectively connected to an extension unit so that they can be unconnected freely. FIG. 6 is a circuit block diagram of the ultrasonic surgical apparatus shown in FIG. 5.

In the first embodiment, one of the handpieces 3A, 3B, and 3C is connected to the main unit 2 at a time. In the embodiment of FIGS. 5 and 6, all three handpieces and the associated hand switches 4 may be connected to the main unit 2 at the same time. In this embodiment, the hand switches 4 are used selectively to operate the handpieces connected to the main unit 2 for different purposes.

In the circuit block diagram of the ultrasonic surgical apparatus of FIG. 6, three lines accommodated in hand switch 4 and foot switch 5 respectively are integrated into one cable. The same reference numerals are assigned to components identical to those shown in FIG. 1 to FIG. 3.

The ultrasonic surgical apparatus 61A of the present embodiment comprised of a main unit 62, a connector extension unit 63, a handpieces 3A, 3B, and 3C, hand switches 4, and a foot switch. A driver for an ultrasonic transducer (not shown) is incorporated in the main unit 62. The connector extension unit 63 is connected to the main unit 62. The handpieces are releasably coupled to connector portions 64a, 64b, and 64c formed on extension unit 63. The hand switches 4 are detachably mounted on the bodies of the operating units of the handpieces. The foot switch 5 is stepped on when selected instead of the hand switches 4.

The main unit 62 is connected to the connector extension unit 63 by way of cables 65a, 65b, and 65c serving as connecting means for transmitting a signal produced by the connector extension unit 63.

The connector extension unit 63 has hand switch connector portions 67a, 67b, and 67c, and three selection switches 68a, 68b, and 68c. The hand switch connectors 21 linked to the three hand switches 4 are joined to the hand switch connector portions 67a, 67b, and 67c. The selection switches 68a, 68b, and 68c serve as selecting means for selecting the three handpieces. Moreover, a foot switch 30 connector portion 69 to which the foot switch connector 22 linked to the foot switch 5 is joined is provided on the back side of the connector extension unit 63. The connector extension unit 63 has the cables 65a, 65b, and 65c extended therefrom. A signal produced by a generating means incorporated in the connector extension unit 63 is transmitted to the main unit 62 by way of the cables 65a, 65b, and 65c serving as connecting means.

Referring to FIG. 6, connectors 8a, 8b, and 8c linked to respective handpieces 3A-3C, and the hand switch connectors 21 linked to the hand switches 4 are coupled to the connector extension unit 63. The connector extension unit 63 is connected to the main unit 62.

The main unit 62 includes a hand switch sensing circuit 71, a foot switch sensing circuit 72, a control unit 73, and an oscillator circuit 74. The hand switch sensing circuit 71 detects signals sent from the hand switches via the connector extension unit 63. The foot switch sensing circuit 72 detects a signal sent from the foot switch 5 via the connector extension unit 63. The control unit 73 outputs a control signal according to signals sent from the switch sensing circuit 71 and foot switch sensing circuit 72. The oscillator circuit 74 drives the handpieces according to a control signal sent from the control unit 73.

The connector extension unit 63 includes a signal generating means, and the cables 65a, 65b, and 65c. The signal generating means generates signals to be transmitted to the three selection switches 68a, 68b, and 68c, which serve as selecting means, and to the main unit 62. The cables 65a, 65b, and 65c serve as transmitting means for transmitting the signals generated by the generating means to the main unit 62.

The generator includes a control circuit 81, a output connector switching relay 82, and a switch sensing circuit 83. The control circuit 81 gives control to supply an output of the oscillator circuit 74 in the main unit 62 to a handpiece selected with any of the selection switches 68a to 68c pressed. The output connector switching relay 82 supplies an output of the oscillator circuit 74 in the main unit to a selected handpiece under the control of the control circuit 81. The switch sensing circuit 83 senses manipulation signals stemming from the hand switches 4 or a manipulation signal stemming from the foot switch 5 via the hand switch connector portions 67a, 67b, and 67c or the foot switch connector portion 69. The switch sensing circuit 83 then produces a signal to be transmitted to the main unit 62.

When the selection switch 68a, is_pressed, the output connector switching relay 82 operates to select the connector joint portion 64a under the control of the control circuit 81. In this state, the switch A or B of the foot switch 5 is stepped on. The switch sensing circuit 83 in the connector extension unit 63 senses a manipulation signal stemming from the foot switch 5. The foot switch sensing circuit 72 in the main unit 62 senses by way of the cable 65b which of the switches A and B of the foot switch 5 has been stepped on. Based on a signal sent from the foot switch sensing circuit 72, the control unit 73 controls activation or inactivation of the oscillator circuit 74. Consequently, power is supplied to the scissors-like handpiece 3A by way of the cable 65a, the output connector switching relay 82 in the connector extension unit 63, the connector joint portion 64a, and the handpiece connector 8a.

Likewise, when the selection switch 68b is pressed, the output connector switching relay 82 operates to select the connector joint portion 64b under the control of the control circuit 81. Consequently, power is supplied to handpiece 3B, and ultrasonic treatment is enabled.

In the above state, that is, when a handpiece to be used is selected by pressing any of the selection switches 68a to 68c, the hand switch 4 is pressed. The switch sensing circuit 83 then senses which of the hand switches has been pressed. The information is transmitted to the control circuit 81, and the output connector switching relay 82 is actuated. Consequently, ultrasonic treatment can be performed using the selected handpiece.

The handpieces can be readily used for different purposes without the necessity of retrofitting the ultrasonic surgical apparatus 61A. The handpieces can be manipulated independently. This leads to improved maneuverability.

For selecting a handpiece by use of the selection switches 68a, 68b, and 68c of the connector extension unit 63 and the hand switches 4, a voice recognition circuit (not shown) for recognizing voice may be included in the connector extension unit 63. A selecting means to be actuated based on the results of voice recognition performed by the voice recognition circuit may be used to select a handpiece. The present invention is not limited to these modes.

Figure 7:
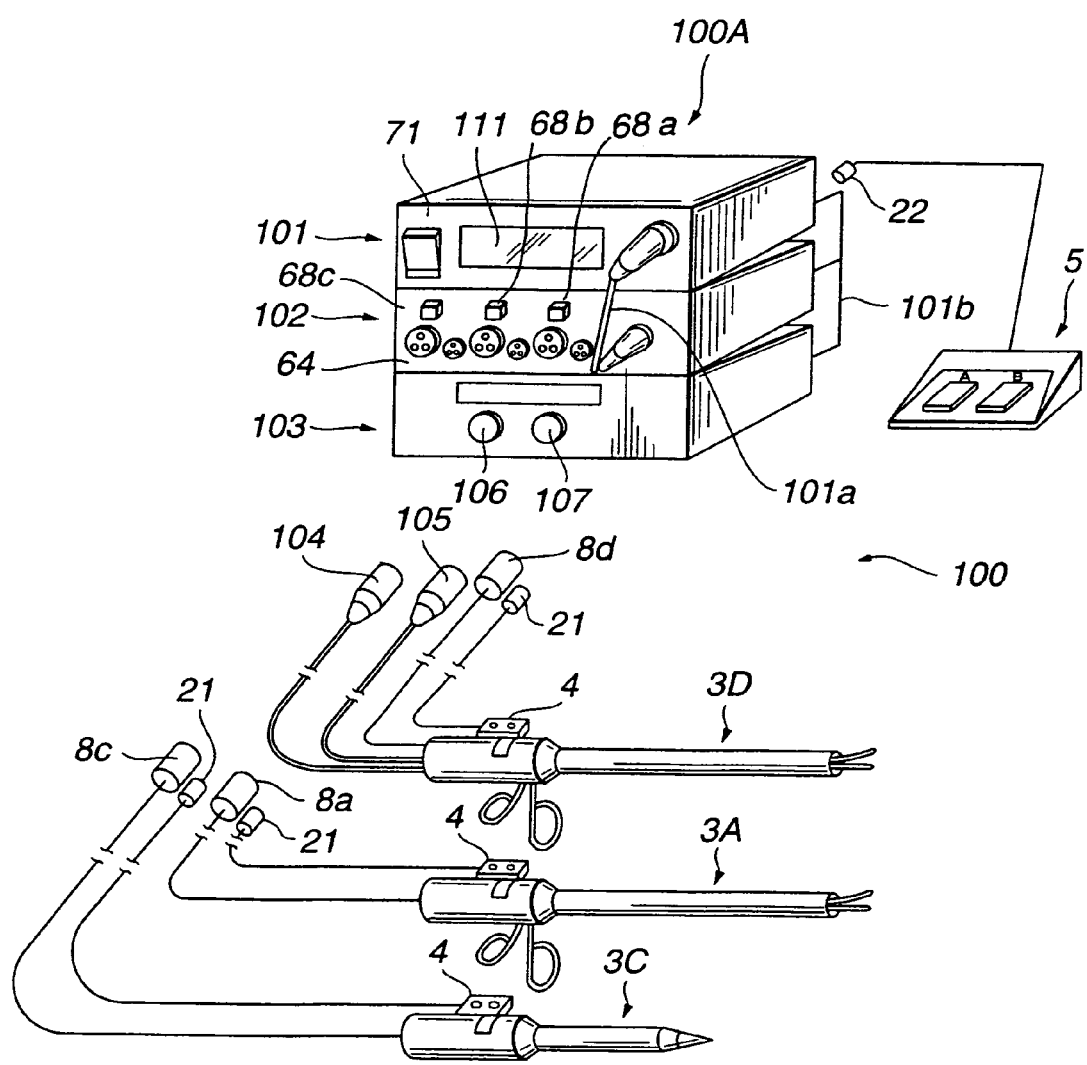
FIG. 7 is an explanatory diagram schematically showing the configuration of third embodiment of an ultrasonic surgical system according to the invention.
Figure 8:
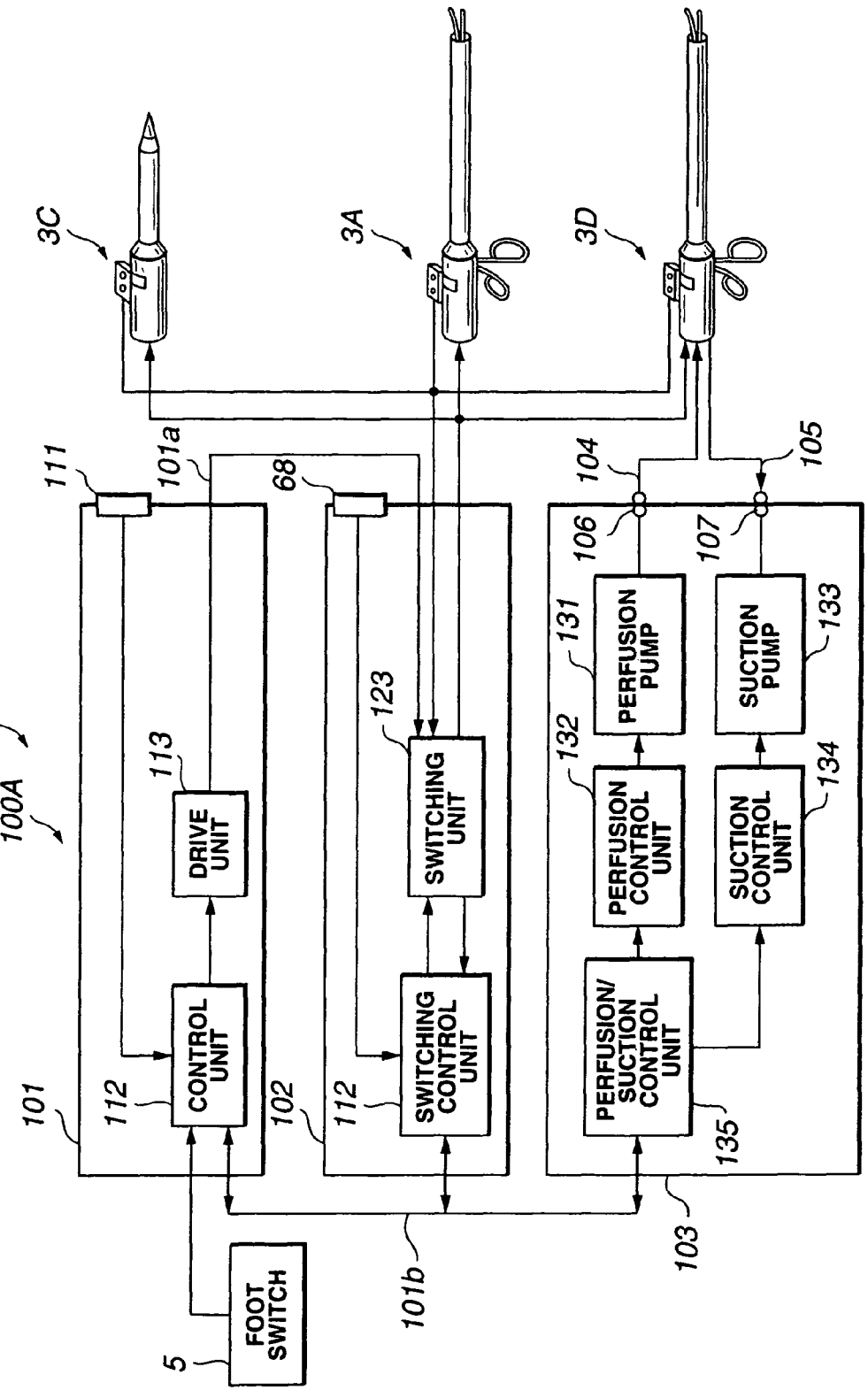
FIG. 8 is a block diagram showing circuitry suitable for use with the ultrasonic surgical system shown in FIG. 7.
Figure 9:
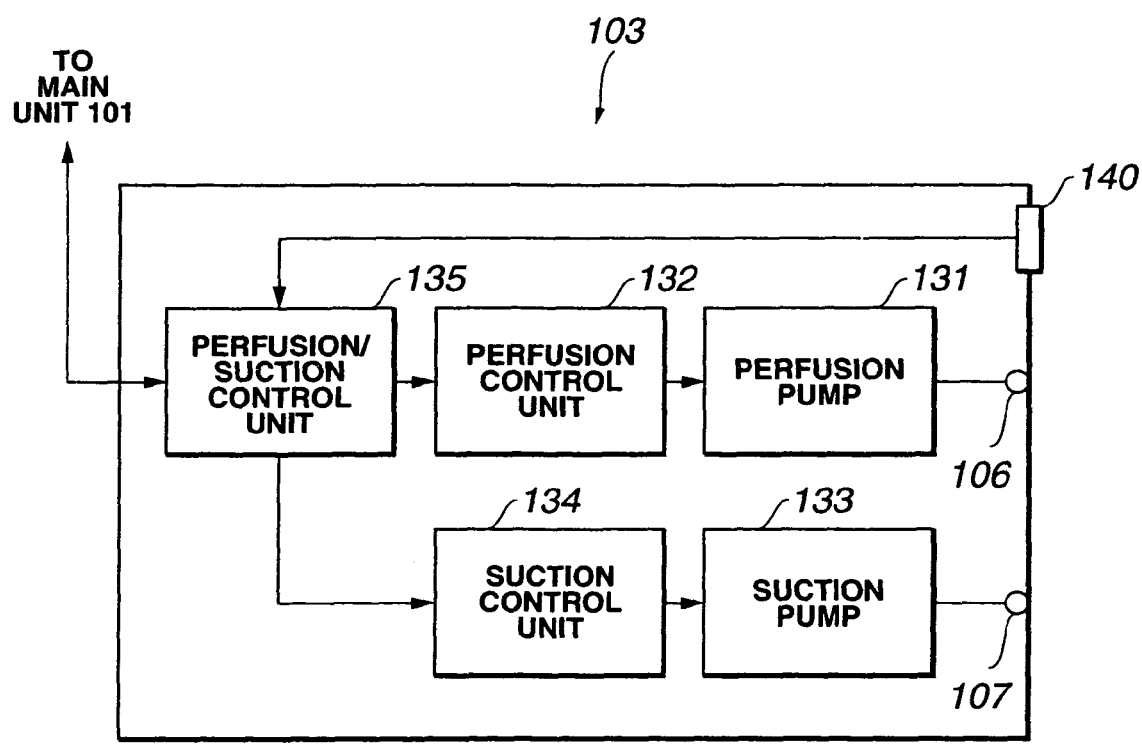
FIG. 9 is a circuit block diagram showing modification of a perfusion suction unit shown in FIG. 8.

FIG. 7 to FIG. 9 relate to the third embodiment. FIG. 7 is an explanatory diagram schematically showing the configuration of an ultrasonic surgical system based on an ultrasonic surgical apparatus having a scissors-like handpiece, a trocar and cannula-like handpiece, and a perfusion/suction handpiece releasably connected to a connector extension unit. FIG. 8 is a circuit block diagram of the ultrasonic surgical apparatus shown in FIG. 7. FIG. 9 is a circuit block diagram of a modification of a perfusion suction unit shown in FIG. 8.

In the second embodiment, the selection switches 68a, 68b, and 68c of the connector extension unit 63 serve as selecting means, the foot switch 5, and the hand switches 4 are used selectively in order to utilize the plurality of handpieces for different purposes. Set values for the respective handpieces are manually input at the main unit 62. The set values, that is, an ultrasonic frequency or a power level are different from handpiece to handpiece. Consequently, the handpieces can be manipulated mutually independently.

In the third embodiment, the selection switches 68 (68a, 68b, and 68c) of the connector extension unit 63 serving as selecting means, the foot switch 5, and the hand switches 4 are used selectively. The set values optimal to the respective handpieces are automatically set.

In the ultrasonic surgical apparatus shown in FIG. 7, the scissors-like handpiece 3D may be an ultrasonic coagulation/incision appliance used to ultrasonically coagulate or incise a lesion. The scissors-like handpiece 3D is provided with a perfusion facility or a suction facility for perfusing a region to be treated in a living tissue or sucking a fluid from the region. The perfusion unit/suction unit is separate from the main extension units. The other components are identical to those shown in FIG. 5 and FIG. 6. The description of the components will be omitted. The same reference numerals are assigned to components identical to those shown in FIG. 5 and FIG. 6.

As shown in FIG. 7, an ultrasonic surgical apparatus 101A for realizing an ultrasonic surgical system 100 comprise a main unit 101, a connector extension unit 102, a perfusion/suction unit 103, a scissors-like handpiece 3A, a trocar and cannula-like handpiece 3C, a perfusion/suction handpiece 3D, hand switches 4, and a foot switch 5. A driver for an ultrasonic transducer (not shown) is incorporated in the main unit 101. The connector extension unit 102 is connected to the main unit 101 by way of a cable 101a and a cable 101b serving as connecting means. The perfusion/suction unit 103 is connected to the main unit 101 by way of the cable 101b and includes a perfusing means and a sucking means. Handpiece 3A, 3C, and 3D are removably connected to respective connector portions 64b, and 64c on the connector extension unit 102. The hand switches 4 are detachably mounted on the bodies of the operating units of the handpieces 3A, 3C, and 3D. The foot switch 5 is stepped on when selected instead of the hand switches 4. Any other handpieces having different shapes from the above handpieces and designed for different purposes may also be used in combination. The handpieces each have an ultrasonic transducer (not shown) incorporated therein.

A panel setting unit 111 serving as a setting means is formed on the front panel 7 of the main unit 101. The panel setting unit 111 is used to set various set values based on the ultrasonic transducers, incorporated in any of the handpieces 3A, 3C, and 3D are driven. The foot switch connector 22 linked to the foot switch 5 is joined to the foot switch connector portion 69 of the main unit 101.

The perfusion/suction handpiece 3D is like handpiece 3A but also includes a perfusion facility or a suction facility The ultrasonic suction appliance pulverizes and emulsifies cells to be removed by utilizing ultrasonic waves, and then sucks and removes the cells. A perfusion channel and a suction channel (not shown) are formed inside the perfusion/suction handpiece 3D. A perfusion tube 164 and a suction tube 105 communicate with the perfusion channel and suction channel respectively. A region to be treated in a living tissue is perfused with fluid provided through a perfusion port, which is not shown, formed in the treatment unit by way of the perfusion tube 104 and perfusion channel in the handpiece 3D. A suction port (also not shown), is formed in the treatment unit by way of the suction tube 105 and suction channel.

The perfusion/suction unit 103 has a perfusion joint portion 106 and a suction joint portion 107 coupled to the perfusion tube 104 and suction tube 105 of the perfusion suction handpiece 3D. Physiological saline or the like used to perfuse a region to be treated in a living tissue is supplied through the perfusion tube 104, or suction pressure used to remove waste material is supplied through the suction tube 105.

Referring to FIG. 8, the hand switches 4 for handpieces 3A, 3C, and 3D are connected to the connector extension unit 102.

The connector extension unit 102 is connected to the main unit 101. The perfusion tube 104 and suction tube 105 of the perfusion suction handpiece 3D are coupled to the perfusion/suction unit 103.

The main unit 101 includes a panel setting unit 112, a drive unit 113, and a control unit 113. The drive unit 113 serves as a driving means for properly driving an ultrasonic transducer (not shown). The control unit 113 serves as a control means for controlling the drive unit 112 and panel setting unit 111.

The extension unit 102 includes of a switching-unit 123 and a switching control unit 122. The switching unit 123 serves as a distributing means for distributing a driving signal, which has been produced by the drive unit 113 in the main unit 101 and received by way of a cable 101a, to the handpieces. The switching control unit 122 controls the switching unit 123. The switching control unit 122 is connected to the selection switches 68. When any of the selection switches 68 is pressed, the switching unit 123 is controlled.

The perfusion/suction unit 103 includes a perfusion pump 131, a perfusion/suction control unit 132, a suction pump 133, a suction pressure control unit 134, and a perfusion/suction control unit 135. The perfusion pump 131 serves as a perfusing means for supplying physiological saline or the like through the perfusion joint portion 106 via the perfusion tube 104. The perfusion control unit 132 drives the perfusion pump 131. The suction pump 133 provides the suction for removing waste material through the suction joint portion 107 via the suction tube 105. The suction pressure control unit 134 controls suction pressure. The perfusion/suction control unit 135 controls the perfusion control unit 132 and the suction pressure control unit 134.

The control unit 112 in the main unit 101 is connected to the switching control unit 122 in the connector extension unit 102 and the perfusion/suction control unit 135 in the perfusion/suction unit 103 over the cable 101b. The control unit 112 transfers information based on various set values set using the panel setting unit 111 to or from the switching control unit 122 and perfusion suction control unit 135. The control unit 112 thus autonomously sets parameters suitable for a selected handpiece. Connectors 8a, 8c, and 8d of respective handpieces 3A, 3C, and 3D are removably coupled respectively to the connector portions 64a, 64b, and 64c on the main unit 101. The different types of handpieces are thus identified mutually independently. A reporting means for identifying a handpiece may be incorporated in each of the connectors 8a, 8c, and 8d of the handpieces. In this case, the reporting means is identified using a judging means implemented in the control unit 112 in the main unit 101. Parameters suitable for a selected handpiece are thus automatically set.

The handpieces 3A, 3C, and 3D are connected to the connector extension unit 102. When one of the hand switch 4 is pressed in order to select a handpiece, the control unit 112 in the main unit 101 is changed over to the connector of the selected handpiece. At the same time, information of the selected type of handpiece is transmitted to the main unit 101. The control unit 112 in the main unit 101 receives the transmitted information. Parameters suitable for the selected handpiece are then transmitted to the drive unit 113 and set therein. At this time, when the perfusion/suction handpiece 3D is used to perform perfusion or suction, the information is sent to the perfusion/suction control unit 135 in the perfusion/suction unit 103. An amount of fluid to be supplied or a level of suction pressure is set at optimal levels under the control of the perfusion/suction control unit 135. Suction pressure is supplied to the handpiece 3D through the suction port 107 via the suction tube 105.

Consequently, selection information concerning a selected one of the plurality of handpieces is transmitted from the main unit 101 to the connector extension unit 102 and perfusion/suction unit 103. Set values optimal to the selected handpiece are then set automatically.

FIG. 9 shows a modification of the perfusion/suction unit 103. Herein, the perfusion suction unit 103 has a setting portion 140 used to set values concerning output of ultrasonic waves. When a handpiece used for perfusion or suction, for example, the perfusion/suction handpiece 3D is selected, values concerning output of ultrasonic waves set at the perfusion/suction unit 103 may be transmitted to the main unit 101 and thus validated. This is useful for a handpiece usable both for ultrasonic coagulation or incision and for ultrasonic emulsification and suction in combination. Furthermore, the connector extension unit 102 may merely send a connector signal to the main unit 101. The main unit 101 may then judge the type of handpiece. The information may be sent from the main unit 101 to the connector extension unit 102 and perfusion/suction unit 103.

Consequently, the plurality of handpieces can be used for different purposes as components of one ultrasonic surgical apparatus. When a handpiece to be used is selected, optimal settings for driving of the handpiece can be set automatically. The ultrasonic surgical system of the present embodiment can thus offer greater maneuverability than the ultrasonic surgical system 61 of the second embodiment.

For selecting a handpiece, the selection switches 68a, 68b, and 68c on the connector extension unit 103 and the hand switches 4 need not be used. Instead, a voice recognition circuit (not shown) for recognizing voice may be incorporated in the connector extension unit 610. A selecting means actuated based on the results of voice recognition performed by the voice recognition 'circuit may be employed, too. The present invention is not limited to these modes.

Figure 11:
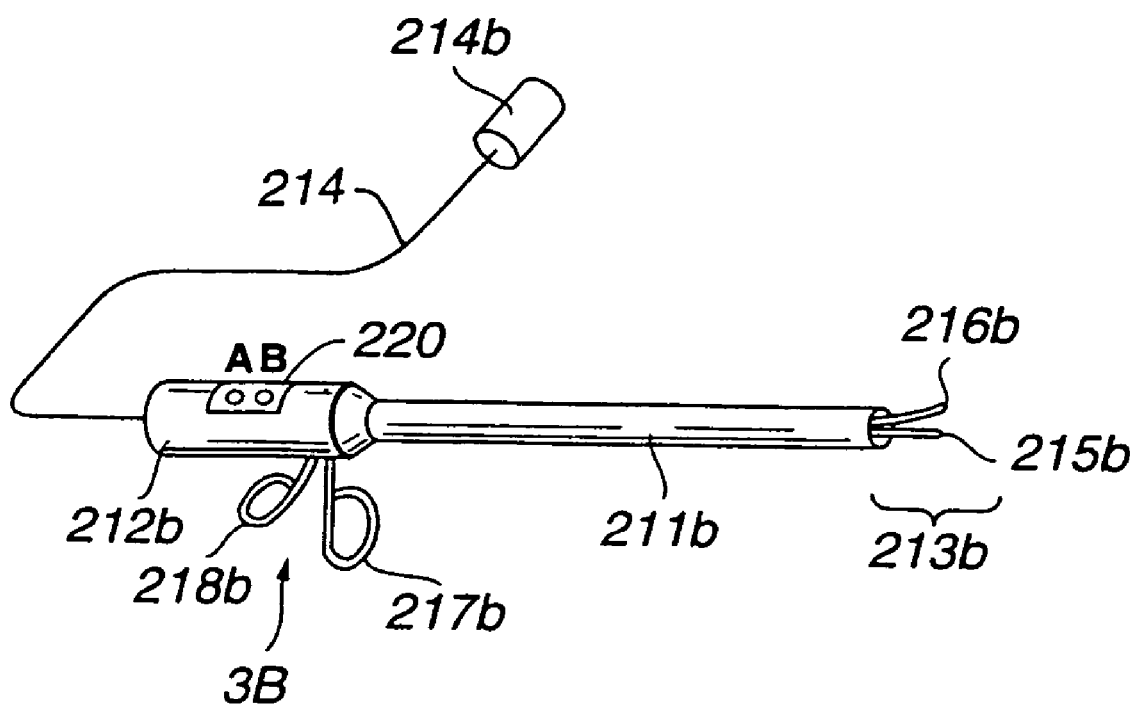
FIG. 11 shows the appearance of a handpiece having a built-in hand switch used when selected instead of a scissors-like handpiece shown in FIG. 10.
Figure 12:
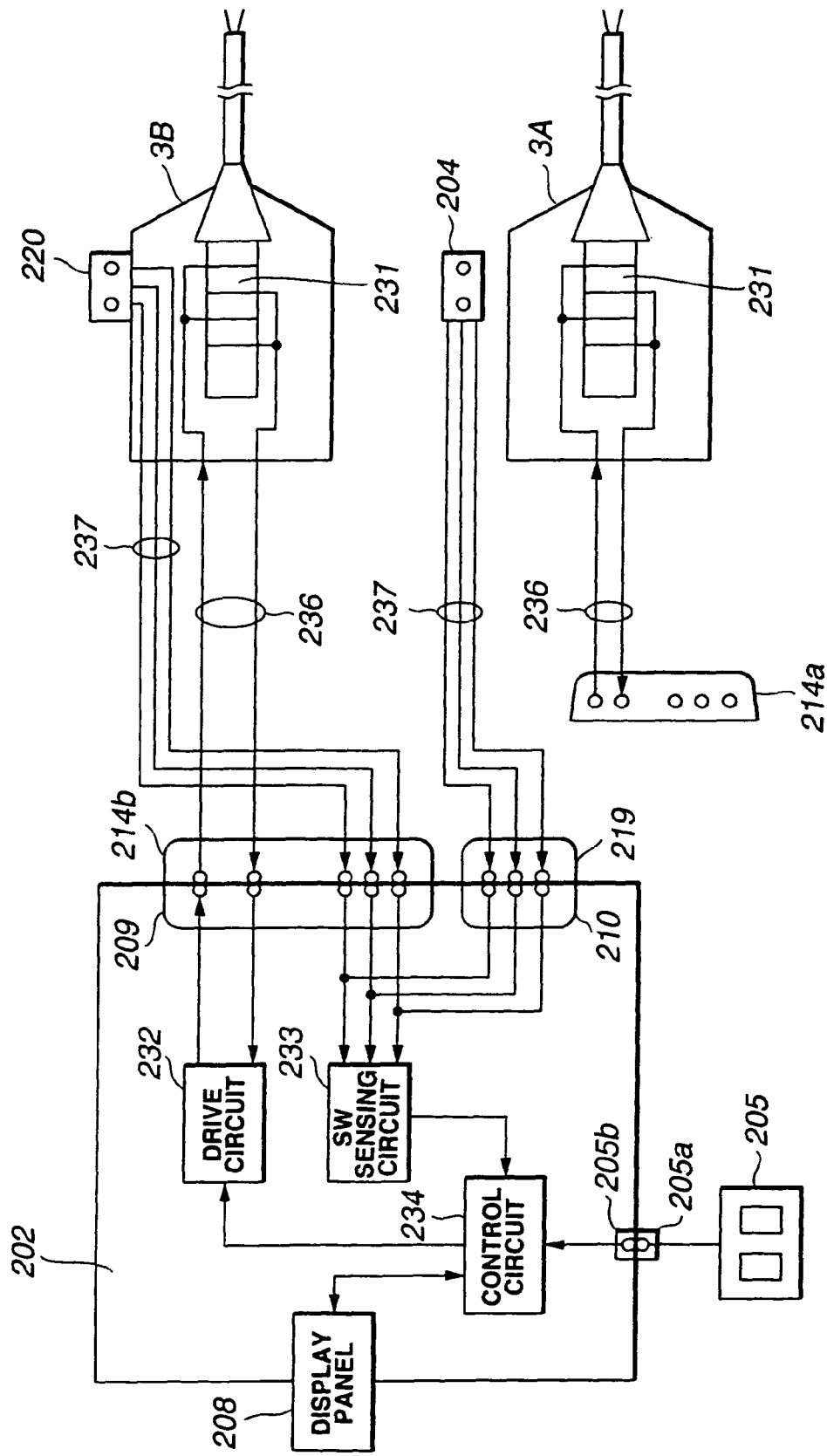
FIG. 12 is a block diagram showing circuitry which may be used with the ultrasonic surgical system shown in FIG. 10.

FIG. 10 is an explanatory diagram schematically showing an ultrasonic surgical system in accordance with the fourth embodiment of the present invention. FIG. 11 shows a handpiece having a built-in hand switch as an alternative to the handpiece shown in FIG. 10. FIG. 12 is a circuit block diagram of the handpiece.

An ultrasonic surgical system 201 of the fourth embodiment includes a main unit 202, a scissors-like handpiece 3A, an external hand switch 4, and a foot switch 205. A driving signal generator for generating a driving signal, which will be described later, is incorporated in the main unit 202. Handpiece 3A is removably coupled to the main unit 202. An ultrasonic transducer that will be described later is incorporated in the scissors-like handpiece 3A. The external hand switch 4 is releasably attached to the body of the operating unit of handpiece 3A. The foot switch 205 is releasably coupled to the main unit 202, and may be used instead of the hand switch 204

A power switch 207, a display panel 208, a handpiece connector 209, and a hand switch connector 210 are provided on front panel 206 of the main unit 202. The display panel 208 indicates a state of operation. The hand-piece connector 209 is connected to handpiece 3A. The external hand switch 204 is connected to the hand switch connector 210. A foot switch connector 205b (see FIG. 12) to which a foot switch plug 205a linked to the foot switch 205 is releasably coupled is located on a rear panel of the main unit 202.

Handpiece 3A is comprised of an elongated sheath 211a, an operating unit 212a, and a treatment unit 213a. The operating unit 212a is coupled to the proximal end of the sheath 211a. The treatment unit 213a is located at the distal end of the sheath 211a. The handpiece 3A has a handpiece plug 214a for connection to the handpiece connector 209 on the main unit 202.

An ultrasonic transducer that will be described later and a probe 215a are incorporated in handpiece 3A. The ultrasonic transducer generates ultrasonic waves. The probe 215a transmits ultrasonic waves from the ultrasonic transducer to the treatment unit 213a. The treatment unit 213a has a clamping portion 216a supported to pivot freely at the distal end of the sheath 211a. The clamping portion 216a can be brought into contact with or separated from the distal part of the probe 215a. The operation unit 212a has a stationary handle 217a and a movable handle 218a. The movable handle 218a is opened or closed relative to the stationary handle 217a, whereby the clamping portion 216a of the treatment unit 213a can be brought into contact with or separated from the distal part of the probe 215a. In this case, when the movable handle 218a is closed, the clamping portion 216a is turned to close relative to the distal part of the probe 215a. The clamping portion 216a and the distal part of the probe 215a cooperate with each other in clamping a living tissue, for example, a blood vessel. The ultrasonic transducer in the handpiece 3A is driven in this state, whereby the living tissue clamped by the probe 215a and the clamping portion 216a is ultrasonically coagulated or incised.

The external hand switch 204 is mounted on operating unit 212a of the handpiece 3A. The hand switch 204 may include two switches A and B. The hand switch plug 219 to be joined to the hand switch connector 210 on the main unit 202 is linked to the proximal end of the hand switch 204.

As an alternative, another handpiece 3B shown in FIG. 11 can be used. This also may be removably connected to the hand switch connector 209 of the main unit 202. The handpiece 3B has a built-in hand switch 220 that is incorporated in operating unit 212b. A signal line from the built-in hand switch 220 included in cable 214 is connected to handpiece plug 214b. The other components are identical to those of handpiece 3A.

In the present embodiment, an output switching device is provided for connecting the driving signal to the transducer in the handpiece. The switching device may be operated by a manipulation signal provided by hand switch 204, or hand switch 220. The driving signal provided at the output port of the handpiece connector 209. In this embodiment, a plurality of handpieces may be connected to a plurality of handpiece connectors 209 on the main unit 202 at the same time. In that event, a switching means may be included to selectively provide a driving signal for the handpiece to be used, through the associated connectors 209.

Next, the circuitry of the ultrasonic surgical system 201 will be described in conjunction with FIG. 12.

The circuitry of the main unit 202 includes a drive circuit 232, a switch sensing circuit 233, and a control circuit 234. The drive circuit 232 drives the ultrasonic transducer 231 incorporated in a handpiece such as 3A or 3B. The switch sensing circuit 233 senses when hand switch 204 (or hand switch 220) has been pressed. The control circuit 234 controls the drive circuit 232 and display panel 208 according to a signal sent from the switch sensing circuit 233, a manipulation signal stemming from the foot switch 203, or a manipulation signal output from the front panel 206.

The handpiece plugs 214a and 214b linked to the handpieces 3A or 3B can be joined to the handpiece connector 209 on the main unit 202. Referring to FIG. 12, handpiece 3B having the built-in hand switch 220 is connected to the main unit 202. The external hand switch 204 is connected to the hand switch connector 210 on the main unit 202.

The handpiece plug 214b accommodates, in addition to a driving signal line 236 routed to the ultrasonic transducer 231, a signal line 237 extending from a hand switch.

In the main unit 202, a signal line 237 extending from the hand switch connector 209 and the signal line 237 extending from the hand switch to the handpiece connector 219 are connected parallel. The switch sensing circuit 233 senses whichever of the external hand switch 204 and built-in hand switch 220 has been pressed, and transmits a signal from the pressed switch to the control circuit 234. The control circuit 234 actuates the drive circuit 232. Thus, output of a driving signal is controlled in order to activate or inactivate the ultrasonic transducer 231. Moreover, the control circuit 234 uses the display panel 208 to indicate a handpiece and hand switch are currently in use, according to a signal sent from the switch sensing circuit 233.

It should be understood, of course, that handpiece 3B or handpiece 3A may be connected directly to the main unit 202.

For example, the switch A or B of the built-in hand switch 220 is pressed. A manipulation signal stemming from the built-in hand switch 220 is then transmitted to the switch sensing circuit 231 in the main unit 2 which recognizes that the switch A or B of the built-in hand switch 220 has been pressed. Based on the sensed manipulation signal, the control circuit 232 controls the drive circuit 232 to control output of a driving signal. The currently used built-in hand switch 220 is indicated on the display panel 208 under the control of the control circuit 232.

In some cases, the external hand switch 204 must be used, for example, when an operator cannot release a handpiece and therefore has to instruct nurse or the like to switch on or off the handpiece. In this case, the external hand switch 204 is connected to the main unit 202 and thus put to use.

When the switch A or B of the external hand switch 204 is pressed, a manipulation signal from the external hand switch 204 is transmitted to the switch sense circuit 231 in the main unit 202 which then recognizes that the external hand switch 204 has been pressed. Based on the sensed manipulation signal, the control circuit 232 controls the drive circuit 232 which provides a driving signal. The currently used external hand switch 204 is indicated on the display panel 208 under the control of the control circuit 232. Alternatively, the external hand switch 4 may be connected to the main unit 202 in advance, and the built-in hand switch 220 may be pressed to control output of the driving signal.

Consequently, whichever of the built-in hand switch 220 and external hand switch 204 is used, the ultrasonic surgical system can be actuated. It can be checked which of the hand switches is used to control output of a driving signal.

This results in the ultrasonic surgical system offering improved maneuverability and enabling remote control despite the simple configuration.

Figure 13:
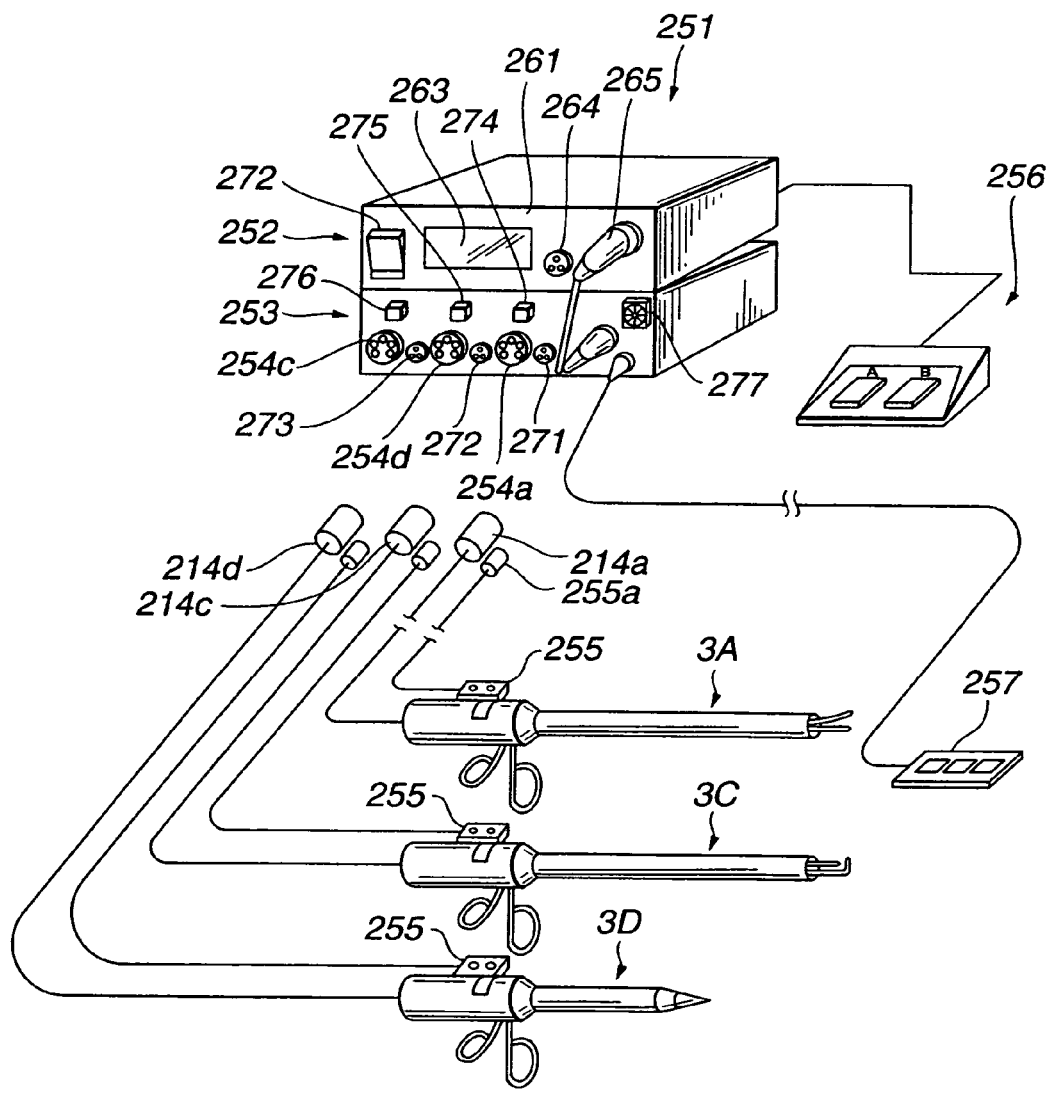
FIG. 13 is an explanatory diagram schematically showing an ultrasonic surgical system in accordance with the fifth embodiment of the present invention.
Figure 14:
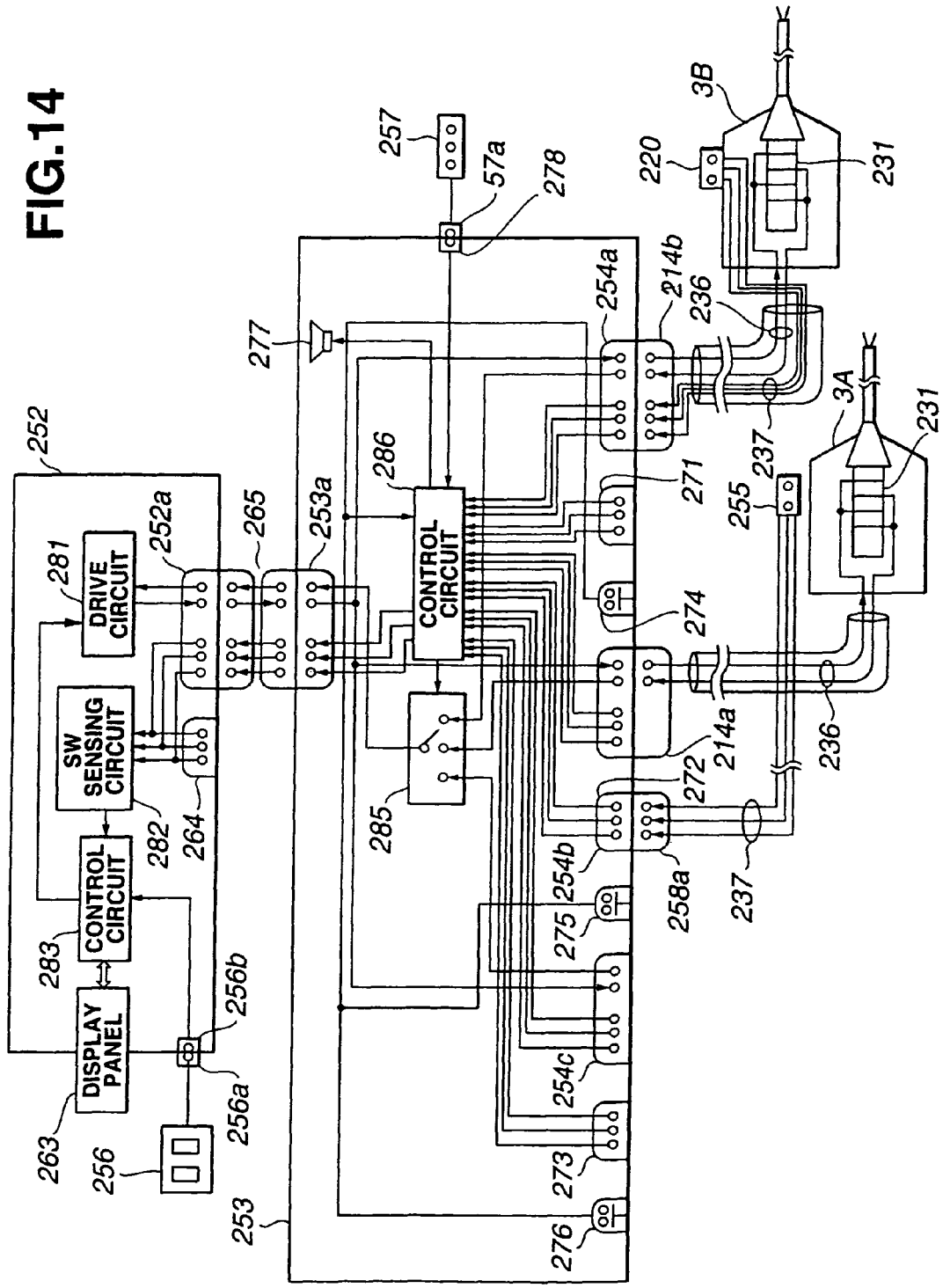
FIG. 14 is a block diagram showing circuitry which may be used with the ultrasonic surgical system shown in FIG. 13.
Figure 15:
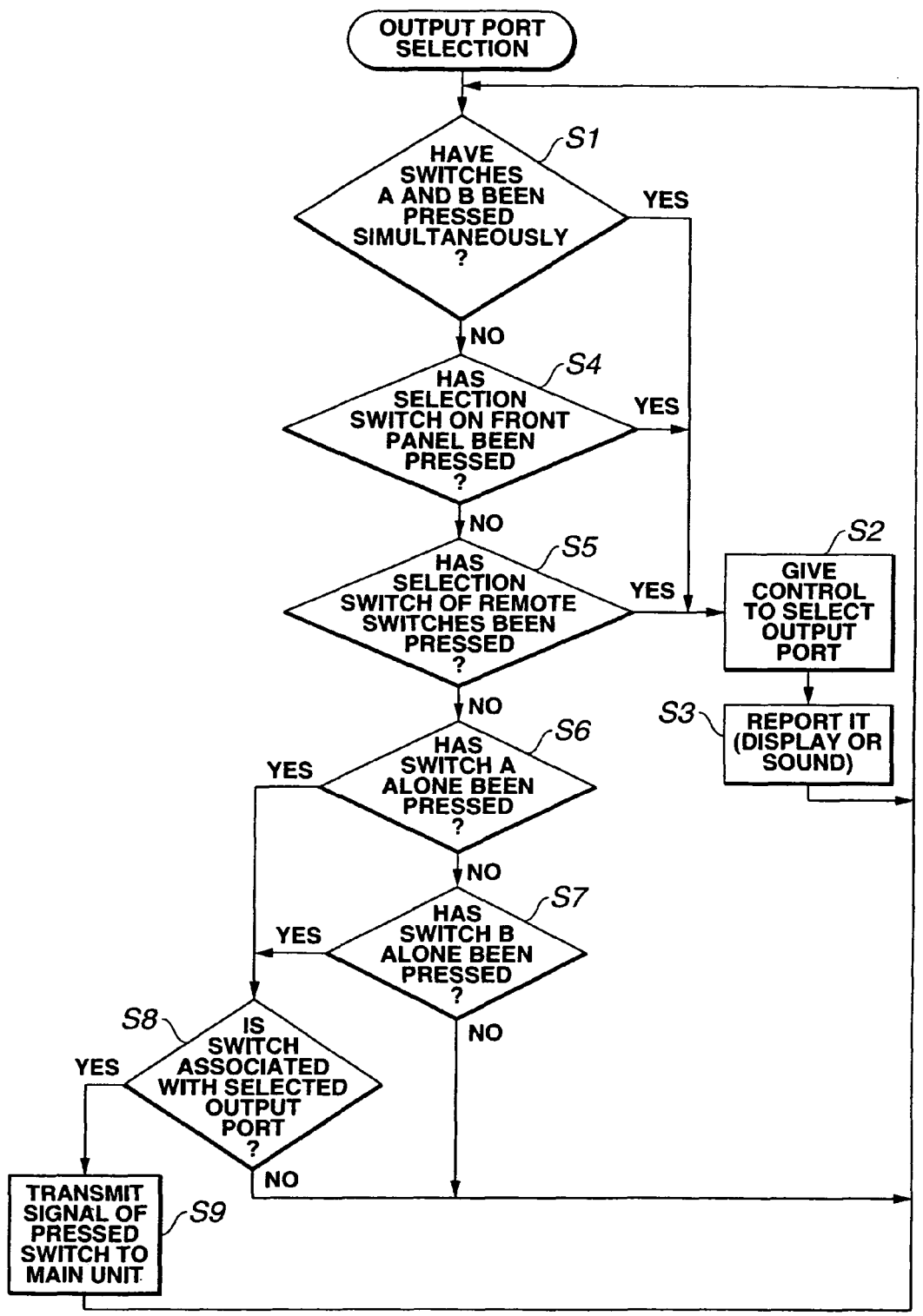
FIG. 15 is a flowchart describing a sequence of selecting a connector of an extension unit shown in FIG. 10.
Figure 16A:
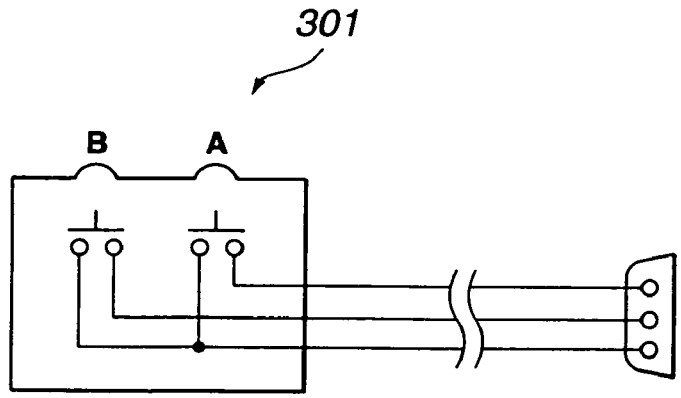
FIG. 16A, FIG. 16B, and FIG. 16C are explanatory diagrams showing the internal wiring of various types of hand switches.
Figure 16B:
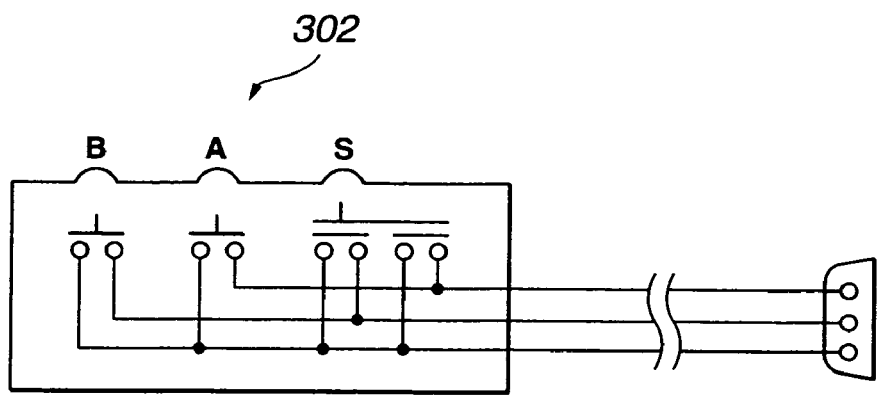
Figure 16C:
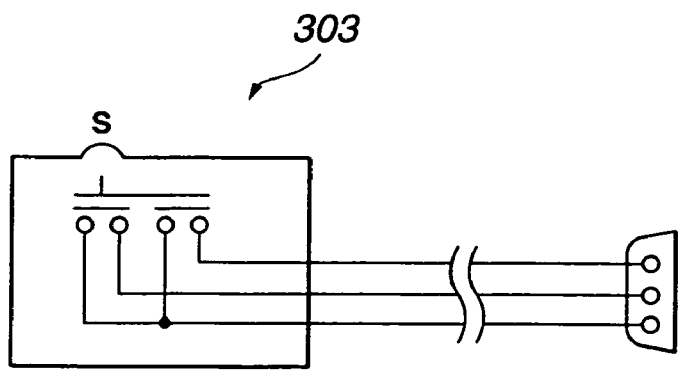

FIG. 13 is an explanatory diagram schematically showing the configuration of an ultrasonic surgical system in accordance with the fifth embodiment of the present invention. FIG. 14 is a circuit block diagram of the ultrasonic surgical system shown in FIG. 13. FIG. 15 is a flowchart describing a sequence of selecting a connector on an extension unit. FIG. 16A to FIG. 16C are explanatory diagrams showing the internal wirings of hand switches. FIG. 16A is an explanatory diagram showing the internal wiring of a hand switch consisting of two output switches A and B. FIG. 16B is an explanatory diagram showing the internal wiring of a hand switch having a selection switch added to the two output switches A and B shown in FIG. 16A. FIG. 16C is an explanatory diagram showing the internal wiring of a hand switch having only the selection switch shown in FIG. 16B.

In the fourth embodiment, the ultrasonic surgical system 201 has one selected handpiece removably connected to the main unit 202. The external hand switch attached to the operating unit of the handpiece or the built-in hand switch 220 is pressed in order to control the handpiece.

By contrast, in the fifth embodiment, an extension unit 253 is used to enable simultaneous connection of a plurality of handpieces. An external hand switch 204 or a built-in hand switch 220 is manipulated in order to select a handpiece employed.

As shown in FIG. 13, an ultrasonic surgical system 251 of the fifth embodiment includes a main unit 252, an extension unit 253, handpieces 3A, and 3D, external hand switches 255, a foot switch 256, and a remote switch 257. A driving signal generator for generating a driving signal that will be described later is incorporated in the main unit 252. The driving signal output from the driving signal generator in the main unit 252 is supplied to the extension unit 253. The handpieces 3A, 3C, and 3D are releasably connected to output ports 254a, 254b, and 254c mounted on the extension unit 253. The hand switches 255 are detachably mounted on the bodies of the operating units of the handpieces. The foot switch 256 may be used instead of the hand switches 255. The remote switch 257 is also releasably connected to the extension unit 253, and may be used to remotely select any of the output ports 254a, 254b, and 254c.

Handpieces 3A, 3C, and 3D have respective handpiece plugs 214a, 214c, and 214d linked thereto. The handpiece plugs 214a, 214c, and 214d are joined to respective output ports 254a, 254b, and 254c. One of the handpieces can be used when selected. Alternatively, a handpiece having a built-in hand switch 220 as described in relation to the fourth embodiment may be used.

A power switch 262, a display panel 263, and a hand switch connector 264 are located on a front panel 261 of the main unit in the same manner as in the fourth embodiment. The display panel 263 indicates an operating state. A hand switch connector 264 is provided to directly connect one of the external hand switch 255 to main unit 242. A foot switch connector 246b (see FIG. 14) to which a foot switch plug 256a linked to the foot switch 256 can be releasably connected is located on the rear panel (not shown) of the main unit 252. Moreover, an output port 252a of the main unit 252 is connected to an input port 253a of the extension unit 253 by way of a connection cord 265 (see FIG. 14). A driving signal that is output from a driving means in the main unit 252 is supplied by way of the output port 252a, connection cord 265, and input port 253a.

Connectors 271, 272, and 273, selection switches 274, 275, and 276, a loudspeaker 277, and a remote switch connector 278 are mounted on the extension unit 253. The connectors 271, 272, and 273 have the same function as the hand switch connector 264 on the main unit 252. The selection switches 274, 275, and 276 are used to manually select one of the output ports 254a, 254b, and 254c. The loudspeaker 277 indicates a selected handpiece and hand switch by producing a suitable sound. The remote switch plug 257a linked to the remote switch 257 is releasably coupled to the remote switch connector 278 (see FIG. 14).

In the present embodiment, a driving signal output from the driving signal generator in the main unit 252 is provided to one of the output ports 254a, 254b, and 254c of the extension unit 253 which is selected using a switching unit included in the extension unit 253 according to a manipulation signal from any of the external hand switches 255 and remote switch 257.

Next, the circuitry of the ultrasonic surgical system of the fifth embodiment will be described in conjunction with FIG. 14.

The construction and operation of the main unit 252 are identical to the main unit 202 described in conjunction with FIG. 12. The main unit 252 is comprised of a drive circuit 281, a switch sense circuit 282, display panel 283, and a control circuit 284.

The circuitry of the extension unit 253 is comprised of a relay 285 for switching the output ports 254a, 254b, and 254c of the extension unit 253 and linking a selected one of the ports to a signal line and a control circuit 286 for controlling the relay 285 according to a manipulation signal stemming from any of the built-in hand switch 220, external hand switches 255, and remote switch 257.

The control circuit 286 has a latch or memory (not shown). When an output port is selected, identification of the selected output port is stored in the latch or memory until another output port is selected.

In the drawing, handpiece 3A with an external switch 255, handpiece 3B having the built-in hand switch 220, the external switches 255, and the remote switch 257 are connected to the extension unit 253.

Any of the built-in hand switch 220, external hand switch 255, or the remote switch 257 may be pressed to select any of the output ports 254a, 254b, and 254c. manipulation signal stemming from pressing of a switch is thus provided to the control circuit 286 in the extension unit 253. The control circuit 286—controls the relay 285 to close a contact thereof linked to the selected output port. The manipulation signal is also transmitted to the switch sensing circuit 282 in the main unit 252.

Hand switches 220 and Hand switches 220 and 255 provide two separate functions, namely selecting the associated handpiece, and providing the drive signal for the transducer of the associated handpiece. When both the switches A and B of a hand switch are pressed at the same time, a signal selecting provided port is output. When either the switch A or B thereof is pressed, a manipulation signal is provided to connect or disconnect the driving signal from the transducer. More particularly, when both the switches A and B of hand switch 220 or 255 are pressed at the same time, a signal for selecting one of the output ports 254a, 254b, and 254c is provided. When either the switch A or B of a switch is pressed, if the switch is associated with an already selected output port, a manipulation signal is provided to control delivery of the driving signal to the transducer.

The selected one output ports 254a, 254b, and 254c is indicated on display panel 208 under the control of the control circuit 286, However, an operator may stand at a position at which he/she cannot see the display panel clearly. As a means for checking which of the output ports has been selected, the control circuit 286 generates a signal which drives the loudspeaker 277 to produce a sound. For example, a single sound is produced when the output port 254a is selected, and produced twice when the output 245a is selected.

Referring to FIG. 15, a description will be made of a sequence of selecting an output port using a built-in hand switch 220 or an external hand switch 255.

For example, if both the switches A and switch B of the built-in hand switch 220 are pressed simultaneously, a signal is provided to the control circuit 286 in the extension unit 253. If it is sensed that the switch A and switch B have been pressed simultaneously (step S1), control is given to select the output port 254a (step S2).

For controlling selection, a signal used to select the output port 254a is transmitted to the switch sense circuit 282 in the main unit 252. The relay 285 is controlled to close a contact thereof linked to the selected output port 254a.

The currently employed handpiece 3B and built-in hand switch 220 are indicated using the display panel 283 under the control of the control circuit 234 in the main unit 252 and the selected output port 254a is reported by a sound produced by loudspeaker 277 under the control of the control circuit 286 in the extension unit 253 (step S3).

Assume now that the switch A and switch B of a hand switch are not pressed simultaneously but the selection switch 274 on the front panel 271 of the extension unit 253 is pressed. A signal is then provided to the control circuit 286 in the extension unit 253, and is sensed that the selection switch 274 has been pressed (step S4). Control is again given to select the output port 254a (step S2), and selected output port 254a is reported (step S3).

When a selection switch of the remote switch 257 associated with the output port 254a is pressed, similarly to when the selection switch 274 on the extension unit 253 is pressed, it is sensed that the selection switch has been pressed (step S5), control is given to select an output port (step S2), and the selected output port is reported (step S3).

By contrast, when either the switch A or switch B of the built-in hand switch 220 is pressed alone, a signal is input to the control circuit 286 in the extension unit 253. If it is sensed that the switch A or switch B has been pressed (step S6 or step S7). If the switch A or switch B is associated with the already selected output port 254a (step S8), the signal stemming from the pressed switch A or switch B is transmitted to the main unit 252 (step S9).

When the output port 254a is selected, a driving signal output from the drive circuit 281 in the main unit 252 is transmitted to handpiece 3B through the selected output port 254a.

Consequently, an operator engaged in an operation can conveniently select a handpiece he/she wants to use, with good maneuverability and minimal distraction. Moreover, when the built-in hand switch 220 is manipulated in order to select a handpiece, the abilities to activate and deactivate the transducer, does not require increasing the number of lines extending from the hand switches. Furthermore, even if the operator cannot see the display panel 263 of the main unit 252, and therefore may not visually confirm switching of the output ports, confirmation will be provided by the sound from the speaker.

Wiring diagrams for hand switches which may be employed in the ultrasonic surgical system have the wirings are shown in FIG. 16A to FIG. 16C.

A hand switch 301 shown in FIG. 16A consists of switches A and B used to enable and disable output.

In comparison with the hand switch 301, a hand switch 302 shown in FIG. 16B is of a type having a selection switch S added to the two output switches A and B. When the switch S is pressed, the switches A and B are turned on simultaneously. The switch S thus acts as a selection switch for selecting an output port with both the switches A and B pressed simultaneously.

The hand switches 301 and 302 provide the abilities to activate and deactivate the handpiece transducer, select an output port. Depending on a handpiece, the built-in hand switch 220 may be used to operate the transducer driver, and another switch such as a foot switch may be used to select an output port. In this case, a hand switch 303 having only the selection switch S as shown in FIG. 16C would prove useful.

In the present invention, it is apparent that a wide range of different embodiments can be constructed based on the foregoing description without departure from the spirit and scope of the invention. Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed:

1. An ultrasonic surgical system comprising:
a plurality of handpieces each having a treatment unit to which a driving signal is supplied to generate energy for treating a patient based on the energy generated, a receiving connector for receiving the driving signal, and a hand switch for generating a manipulation instruction signal to generate energy for treating the patient;
a main unit including a drive unit for generating the driving signal for the plurality of handpieces to generate the energy, a control unit for controlling the drive unit, and a handpiece connector operative to connect the receiving connector to output the driving signal generated by the drive unit to the handpiece;
a connector expansion unit including a driving signal input connector receiver for receiving the driving signal from the main unit, the driving signal input connector receiver being connectable to the handpiece connector via a connecting cable, a plurality of handpiece connectors for connecting to the receiving connectors of the plurality of handpieces respectively to supply the driving signal from the driving signal input connector receiver to the plurality of handpieces, a switch for switching the driving signal received by the driving signal input connector receiver to one of the plurality of handpiece connectors, a switching control unit for controlling the switch, and a switch detecting unit to input the manipulation instruction signal generated by the operation of the hand switch provided to the handpiece switched to by the switch among the plurality of handpieces and detect the manipulation instruction of the handpiece, the detected manipulation instruction signal being supplied to the control unit of the main unit so that the drive unit is driven by the control signal from the control unit to generate the driving signal; and
a handpiece drive signal supplying cable including a receiving connector for each of the plurality of handpieces connected to the plurality of handpiece connectors for supplying the driving signal connected to the switch of the expansion unit, wherein
the receiving connector provided to the handpiece drive signal supplying cable includes a reporting unit for identifying and notifying a type of the connected handpiece, and the control unit of the main unit is configured to recognize a notification from the reporting unit to judge the type of the connected handpiece and to automatically set an operating parameter corresponding to the connected handpiece.

2. The surgical system according to claim 1, wherein at least one of the handpieces has a perfusion path and a suction path, and the surgical system further comprises a perfusion/suction unit having a perfusion part and a suction part communicating with the perfusion path and the suction path of the handpiece, connected to the control unit of the main unit via a control signal transmitting cable.

3. An ultrasonic surgical system comprising:
a plurality of handpieces each having a treatment unit to which a driving signal is supplied to generate energy for treating a patient based on the energy generated, a receiving connector for receiving the driving signal, and a hand switch for generating a manipulation instruction signal to generate energy for treating the patient, at least one of the handpieces also having a perfusion path and a suction path;

a main unit including a drive unit for generating the driving signal for the plurality of handpieces to generate the energy, a control unit for controlling the drive unit, and a handpiece connector operative to connect the receiving connector to output the driving signal generated by the drive unit to the handpiece;

a perfusion/suction unit having a perfusion part and a suction part communicating with the perfusion path and the suction path of the at least one handpiece, connected to the control unit of the main unit via a control signal transmitting cable;

a connector expansion unit including a driving signal input connector receiver for receiving the driving signal from the main unit, the driving signal input connector receiver being connectable to the handpiece connector via a connecting cable, a plurality of handpiece connectors for connecting to the receiving connectors of the plurality of handpieces respectively to supply the driving signal from the driving signal input connector receiver to the plurality of handpieces, a switch for switching the driving signal received by the driving signal input connector receiver to one of the plurality of handpiece connectors, a switching control unit for controlling the switch, and a switch detecting unit to input the manipulation instruction signal generated by the operation of the hand switch provided to the handpiece switched to by the switch among the plurality of handpieces and detect the manipulation instruction of the handpiece, the detected manipulation instruction signal being supplied to the control unit of the main unit so that the drive unit is driven by the control signal from the control unit to generate the driving signal; and a handpiece drive signal supplying cable including a receiving connector for each of the plurality of handpieces connected to the plurality of handpiece connectors for supplying the driving signal connected to the switch of the expansion unit;

wherein the receiving connector provided to the handpiece drive signal supplying cable is configured to enable identifying a type of the connected handpiece, and the control unit of the main unit is configured to identify the type using the type-identifying capability of the connected handpiece and to automatically set an operating parameter corresponding to the connected handpiece, and the perfusion/suction unit has an operation parameter setting unit for setting the operation parameter for controlling the operating condition of the drive unit corresponding to the handpiece in accordance with the energy generated in the handpiece.

4. The surgical system according to claim 3, further comprising: the control signal transmitting cable to connect between a control signal output part of the main unit and a control signal input part of the connector expansion unit and operative to connect the control unit of the main unit and the switching control unit of the connector expansion unit.

5. The surgical system according to claim 3, wherein the connector expansion unit further comprises: a plurality of selection switches for operating a handpiece selected among the plurality of handpieces, the plurality of selection switches being provided in correspondence with the plurality of handpieces, the selection switches activating the switching unit for switching.

6. The surgical system according to claim 3, further comprising: an operation parameter setting unit for setting operation parameters for controlling the operating condition of the drive unit in correspondence with each of the handpieces in accordance with the energy generated in each of the plurality of handpieces.

7. The surgical system according to claim 6, wherein the control unit links information of types of the plurality of handpieces connected to the plurality of handpiece connectors for supplying driving signals of the connector expansion unit and the operation parameter of each of the plurality of handpieces set by the operation parameter setting unit and controlling the treating condition of the handpiece based on the operation parameter in correspondence with the activated handpiece among the plurality of handpieces.

8. The surgical system according to claim 3, wherein the perfusion/suction unit includes a perfusion pump, a perfusion control part to control the perfusion pump, a suction pump, and a suction control part to control the suction pump.

9. The surgical system according to claim 3, wherein an operation parameter setting unit is provided, the operation parameter setting unit being operative to provide an operation parameter setting for the perfusion pump and the suction pump, the operation parameter for the perfusion pump and the suction pump including a fluid pressure level for the perfusion pump and a suction pressure for the suction pump.

10. The surgical system according to claim 3, wherein the receiving connector of the handpiece connected to each of the plurality of handpiece connectors for supplying driving signals of the connector expansion unit comprises a function that identifies the type of the connected handpiece and automatically sets the fluid pressure level for the perfusion pump and the suction pressure for the suction pump corresponding to the connected handpiece.

11. The surgical system according to claim 3, wherein the switching control unit includes a switching part for switching operative to switch the driving signal input from the driving signal input connector receiver supplied to any one of the plurality of handpieces, and a control part for switching to control the switching part.

\* \* \* \* \*